United States Patent
Liou et al.

(10) Patent No.: US 8,119,683 B2
(45) Date of Patent: Feb. 21, 2012

(54) ARYL SUBSTITUTED SULFONAMIDE COMPOUNDS AND THEIR USE AS ANTICANCER AGENTS

(75) Inventors: Jing-Ping Liou, Taipei (TW); Jang-Yang Chang, Taipei (TW)

(73) Assignees: Taipei Medical University, Taipei (TW); DCB-USA LLC, Wilmington, DE (US); National Health Research Institutes, Zhunan Town (TW)

( * ) Notice: Subject to any disclaimer, the term of this patent is extended or adjusted under 35 U.S.C. 154(b) by 0 days.

(21) Appl. No.: 12/852,755

(22) Filed: Aug. 9, 2010

(65) Prior Publication Data

US 2011/0039880 A1    Feb. 17, 2011

Related U.S. Application Data

(60) Provisional application No. 61/232,601, filed on Aug. 10, 2009.

(51) Int. Cl.
C07D 209/04 (2006.01)
A01N 43/38 (2006.01)
A61K 31/405 (2006.01)

(52) U.S. Cl. ....................... 514/415; 548/509
(58) Field of Classification Search ............... 514/415; 548/509
See application file for complete search history.

(56) References Cited

U.S. PATENT DOCUMENTS 7,741,495 B2 * 6/2010 Liou et al. .................. 548/469

FOREIGN PATENT DOCUMENTS

| GB | 2441396 | * | 3/2008 |
| KR | 10-2008-0020566 | | 3/2008 |
| WO | WO2009/070645 | | 6/2009 |

OTHER PUBLICATIONS

Wang, M. et al. "Synthesis of new carbon-11-labeled 7-aroyl-aminoidoline 1-sulfonamides as potential PET agents for imaging of tubulin polymerization in cancers"; Journal of Labelled Compounds and Radiopharmaceuticals; 51:6-11; (2008).

Liou, J, et al. "A Novel Oral Indoline-Sulfonamide Agent, N-[1-(4-Methoxybenzenesulfonyl)-2,3-dihydro-1H-indol-7-yl]-Isonicotinamide (J30), Exhibits Potent Activity against Human Cancer Cells in Vitro and in Vivo Through the Disruption of Microtuble"; The Journal of Pharmacology and Experimental Therapeutics; 323(1):398-405 (2007).

Morgan R.E. et al.; "Inhibitors fo Tubulin Assembly Identified through Screening a Compound Library"; Chemical Biology & Drug Design; 72:513-524 (2008).

Lai, M. et al.; "Synthesis and Structure-Activity Relationships of 1-Benzyl-4,5,6-trimethoxyindoles as a Novel Class of Potent Antimitotic Agents"; ChemMedChem; 4:588-593 (2009).

* cited by examiner

*Primary Examiner* — Janet Andres
*Assistant Examiner* — Niloofar Rahmani
(74) *Attorney, Agent, or Firm* — Occhiuti Rohlicek & Tsao LLP

(57) ABSTRACT

Aryl substituted sulfonamide compounds of formula (I):

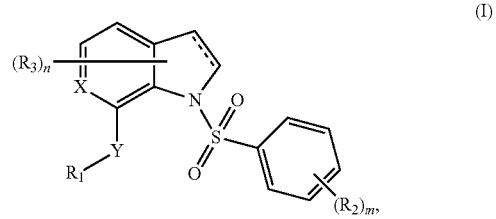

wherein ---- bond, X, Y, $R_1$, $R_2$, $R_3$, m, and n are defined herein. Also disclosed is a method for treating cancer with these compounds.

10 Claims, No Drawings

ARYL SUBSTITUTED SULFONAMIDE COMPOUNDS AND THEIR USE AS ANTICANCER AGENTS

CROSS REFERENCE TO RELATED APPLICATIONS

This application claims the benefit of the priority pursuant to 35 U.S.C. §119(e) of U.S. Provisional Application Ser. Nos. 61/232,601, filed Aug. 10, 2009, the content of which is incorporated herein by reference.

BACKGROUND

Microtubules are intracellular tubes composed of α- and β-tubulins. As important components of cytoskeleton, they play important roles in, among others, cell division, which is essential to cancer development. Thus, microtubules/tubulins have attracted great attention as targets of cancer therapy.

SUMMARY

This invention is based on the unexpected discovery that certain aryl substituted sulfonamide compounds inhibit tubulin polymerization and have potent anticancer activity. Thus, this invention relates to aryl substituted sulfonamide compounds and their use in cancer treatment.

In one aspect, this invention features an aryl substituted sulfonamide compound of formula (I):

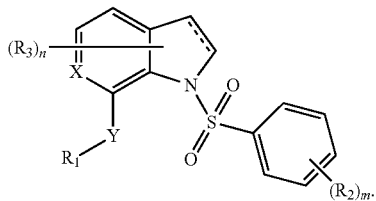

(I)

In this formula, ⸺ bond is a single bond or a double bond; X is N or $CR_a$, in which $R_a$ is H, alkyl, alkenyl, alkynyl, aryl, heteroaryl, cycloalkyl, cycloalkenyl, heterocycloalkyl, or heterocycloalkenyl; Y is deleted or is $NR_b$, in which $R_b$ is H, alkyl, alkenyl, alkynyl, aryl, heteroaryl, cycloalkyl, cycloalkenyl, heterocycloalkyl, or heterocycloalkenyl; $R_1$ is aryl, heteroaryl, cycloalkyl, cycloalkenyl, heterocycloalkyl, or heterocycloalkenyl if Y is deleted or if Y is $NR_b$ and the ⸺ bond is a single bond; or $R_1$ is alkyl, alkenyl, alkynyl, aryl, heteroaryl, cycloalkyl, cycloalkenyl, heterocycloalkyl, or heterocycloalkenyl if Y is $NR_b$ and the ⸺ bond is a double bond; $R_2$ is alkenyl, alkynyl, aryl, heteroaryl, cycloalkyl, cycloalkenyl, heterocycloalkyl, heterocycloalkenyl, halo, cyano, nitro, $OR_c$, $SO_2NR_cR_d$, $OC(O)R_c$, $C(O)R_c$, $C(O)OR_c$, $C(O)NR_cR_d$, $NR_cR_d$, $NHC(O)R_c$, $NHC(O)NR_cR_d$, or $NHC(S)R_c$, in which each of $R_c$ and $R_d$, independently, is H, alkyl, alkenyl, alkynyl, aryl, heteroaryl, cycloalkyl, cycloalkenyl, heterocycloalkyl, or heterocycloalkenyl; $R_3$ is alkyl, alkenyl, alkynyl, aryl, heteroaryl, cycloalkyl, cycloalkenyl, heterocycloalkyl, heterocycloalkenyl, halo, cyano, nitro, $OR_c$, $SO_2NR_cR_d$, $OC(O)R_c$, $C(O)R_c$, $C(O)OR_c$, $C(O)NR_cR_d$, $NR_cR_d$, $NHC(O)R_c$, $NHC(O)NR_cR_d$, or $NHC(S)R_c$; m is 0, 1, 2, 3, 4, or 5; and n is 0, 1, 2, 3, 4, 5, or 6.

One subset of the above-described aryl substituted sulfonamide compounds includes those of formula (II):

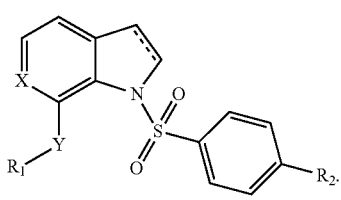

(II)

In these compounds, Y can be deleted or NH; X can be CH or N; $R_1$ can be aryl (e.g., phenyl), or heteroaryl (e.g., furyl, pyridyl, or thienyl), each optionally substituted with halo, haloalkyl, amino, aminoalkyl, hydroxy, alkoxy, cyano, nitro, CHO, carboxyl or acyl; or $R_2$ can be OR (e.g., in which $R_c$ is alkyl) or $SO_2NR_cR_d$.

Another subset of the above-described aryl substituted sulfonamide compounds includes those in which $R_2$ is $OR_c$ or $SO_2NR_cR_d$. In these compounds, $R_1$ can be aryl (e.g., phenyl), or heteroaryl (e.g., furyl, pyridyl, or thienyl), each optionally substituted with halo, haloalkyl, amino, aminoalkyl, hydroxy, alkoxy, cyano, nitro, CHO, carboxyl or acyl; Y can be deleted or NH; or X can be CH or N.

The term "alkyl" refers to a straight or branched monovalent hydrocarbon containing, unless otherwise stated, 1-20 carbon atoms (e.g., $C_1$-$C_{10}$). Examples of alkyl include, but are not limited to, methyl, ethyl, n-propyl, i-propyl, n-butyl, i-butyl, and t-butyl. The term "alkenyl" refers to a straight or branched monovalent hydrocarbon containing 2-20 carbon atoms (e.g., $C_2$-$C_{10}$) and one or more double bonds. Examples of alkenyl include, but are not limited to, ethenyl, propenyl, allyl, and 1,4-butadienyl. The term "alkynyl" refers to a straight or branched monovalent hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "amino" refers to $NH_2$, alkylamino, or arylamino. The term "alkylamino" refers to an —N(R)— alkyl radical in which R can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, 1,4-cyclohexylene, cycloheptyl, cyclooctyl, and adamantyl. The term "cycloalkenyl" refers to a monovalent non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a monovalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, tetrazol, and thiazolyl.

Alkyl, alkenyl, alkynyl, cycloalkyl, heterocycloalkyl, cycloalkenyl, heterocycloalkenyl, amino, aryl, and heteroaryl mentioned above include both substituted and unsubstituted moieties. Possible substituents on amino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)NH$_2$), carboxyl (—COOH), and carboxylic ester. On the other hand, possible substituents on alkyl, alkenyl, alkynyl, or alkylene include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The aryl substituted sulfonamide compounds described herein include the compounds themselves, as well as their salts, their solvates, and their prodrugs, if applicable. A salt, for example, can be formed between an anion and a positively charged group (e.g., amino) on an aryl substituted sulfonamide compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on an aryl substituted sulfonamide compound. Suitable cations include sodium ion, potassium ion, magnesium ion, calcium ion, and an ammonium cation such as tetramethylammonium ion. The aryl substituted sulfonamide compounds also include those salts containing quaternary nitrogen atoms. Examples of prodrugs include esters and other pharmaceutically acceptable derivatives, which, upon administration to a subject, are capable of providing active aryl substituted sulfonamide compounds.

In another aspect, this invention relates to a method for inhibiting tubulin polymerization by contacting a cell with an effective amount of an aryl substituted sulfonamide compound described above.

In yet another aspect, this invention relates to a method for treating cancer by administering to a subject in need thereof an effective amount of an aryl substituted sulfonamide compound described above.

Also within the scope of this invention is a pharmaceutical composition containing one or more of the above-described aryl substituted sulfonamide compounds for use in treating cancer, as well as this therapeutic use and use of the compounds for the manufacture of a medicament for treating cancer.

The details of one or more embodiments of the invention are set forth in the description below. Other features, objects, and advantages of the invention will be apparent from the description and the claims.

DETAILED DESCRIPTION

Shown below are exemplary compounds described herein:

Compound 1

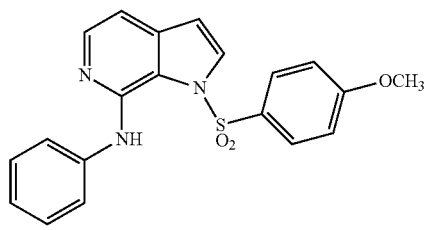

Compound 2

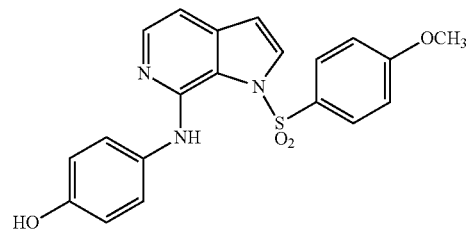

Compound 3

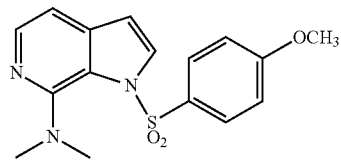

Compound 4

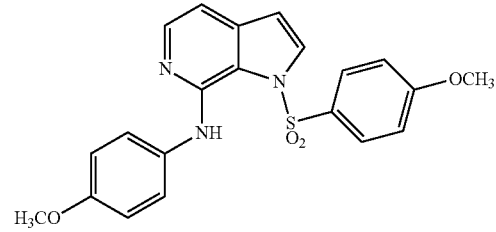

Compound 5

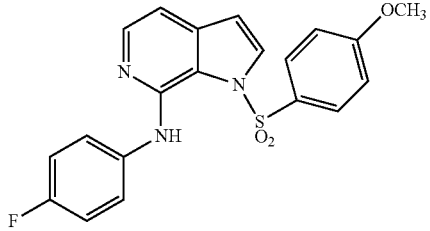

Compound 6

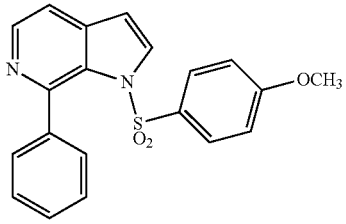

Compound 7
Compound 8
Compound 9
Compound 10
Compound 11
Compound 12
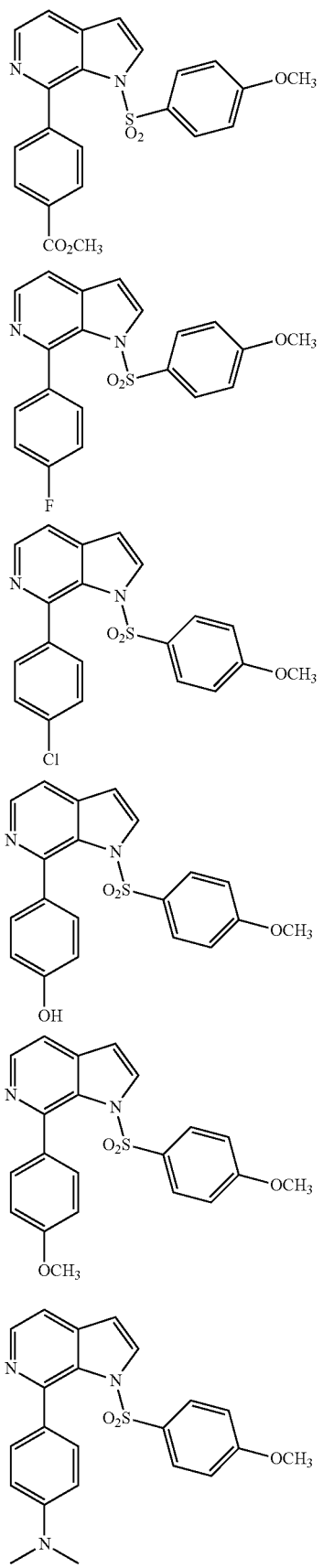
Compound 13
Compound 14
Compound 15
Compound 16
Compound 17
Compound 18
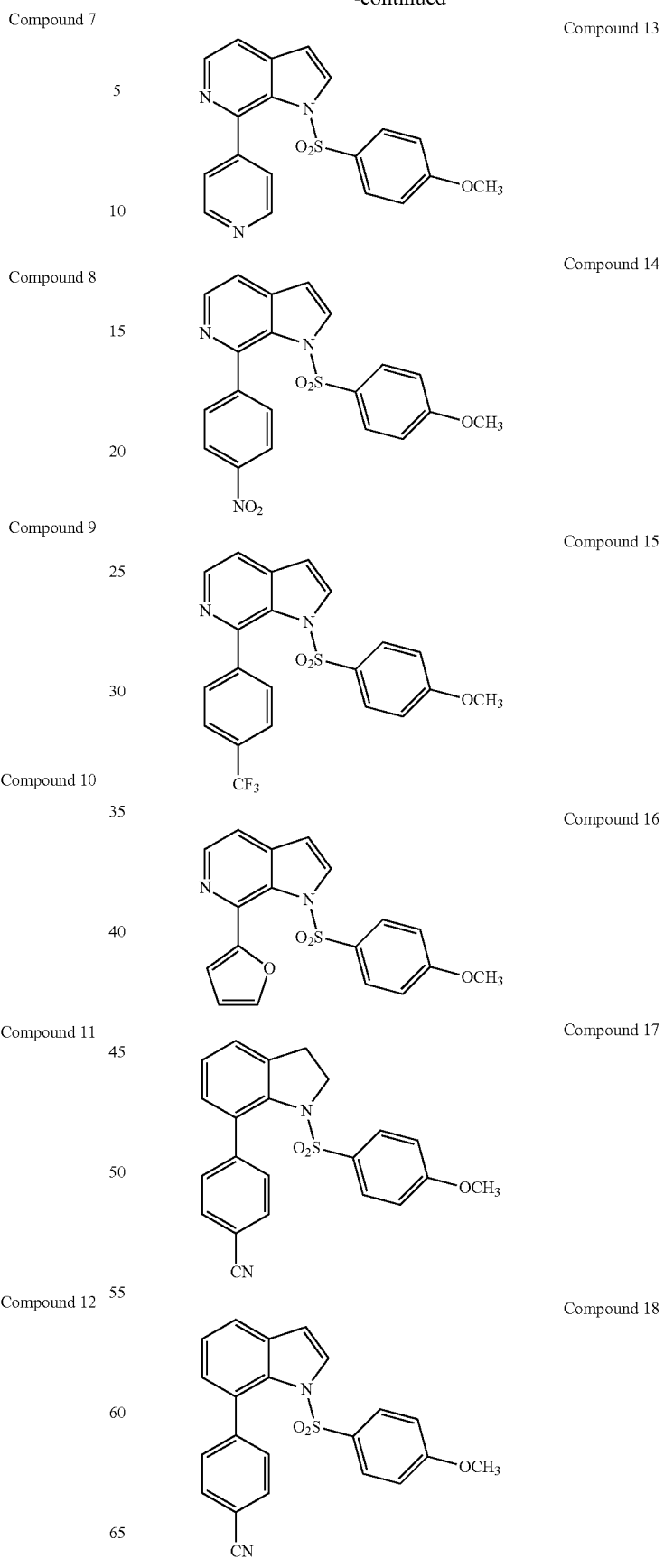

Compound 19
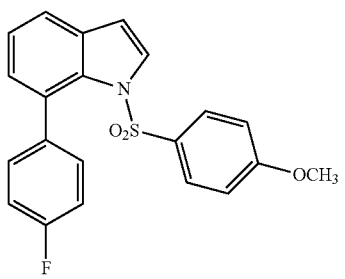
Compound 20
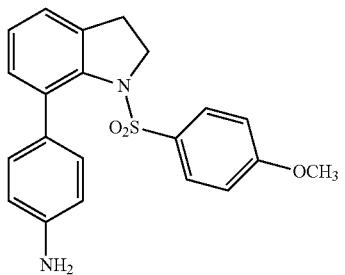
Compound 21
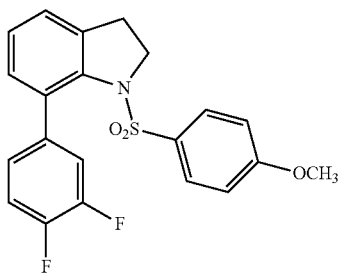
Compound 22
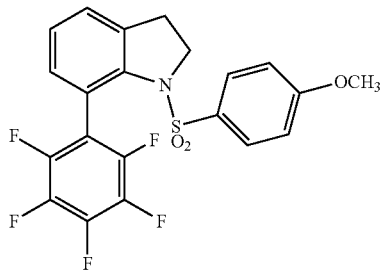
Compound 23
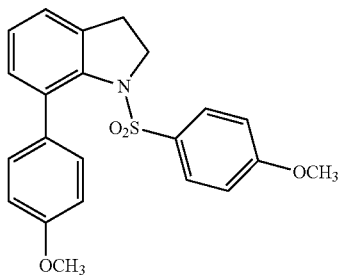
Compound 24
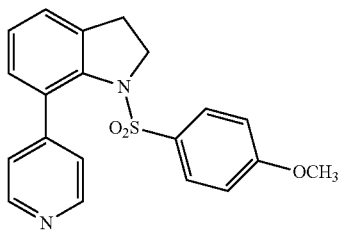
Compound 25
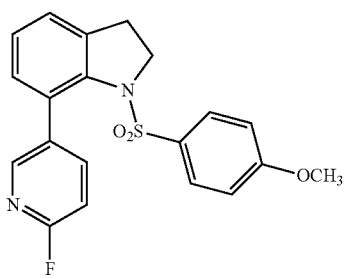
Compound 26
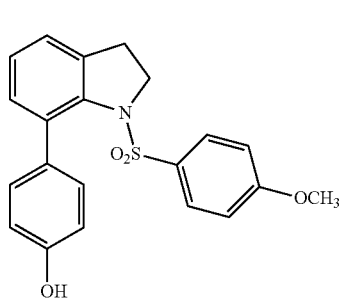
Compound 27
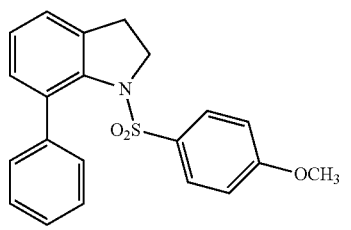
Compound 28
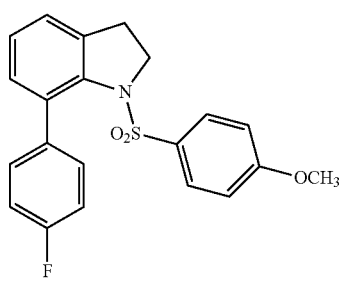
Compound 29
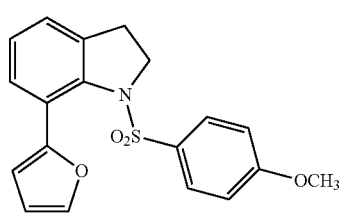
Compound 30

Compound 31
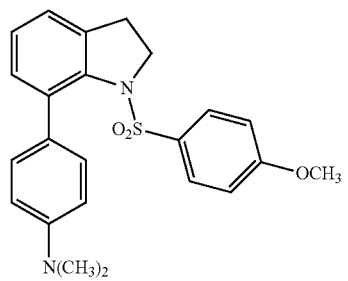
Compound 32
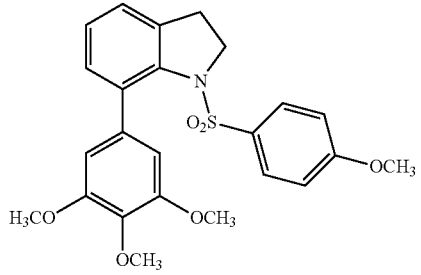
Compound 33
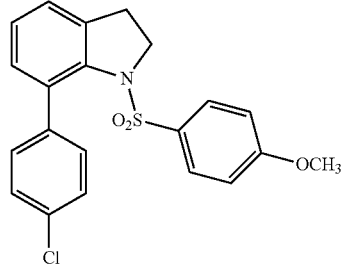
Compound 34
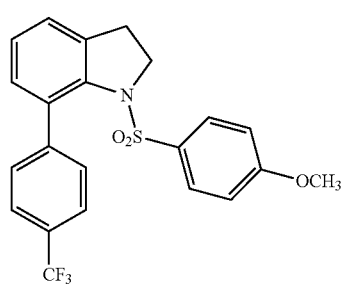
Compound 35
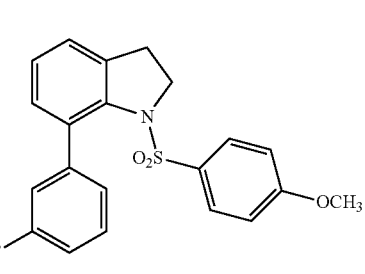
Compound 36
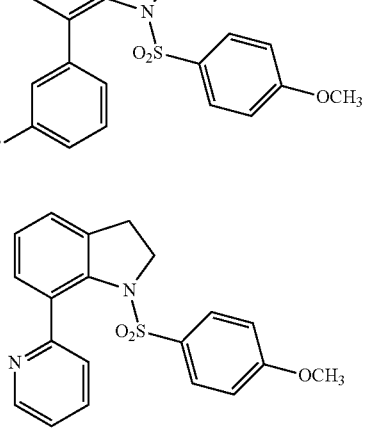
Compound 37
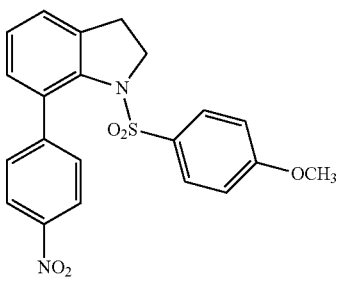
Compound 38
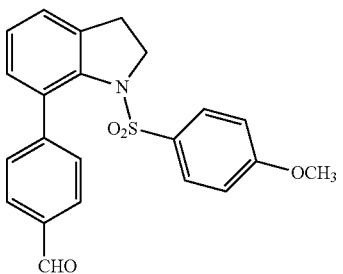
Compound 39
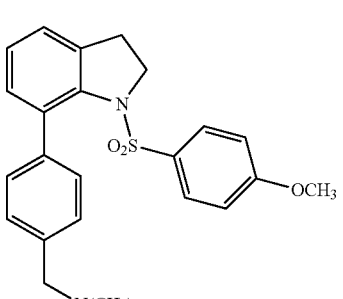
Compound 40
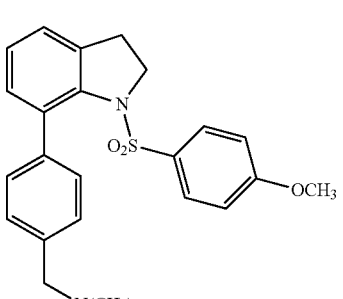
Compound 41
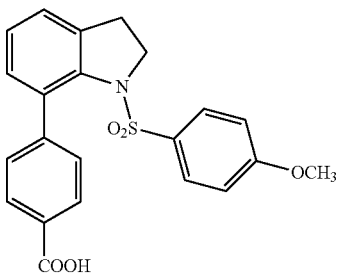

-continued

Compound 42

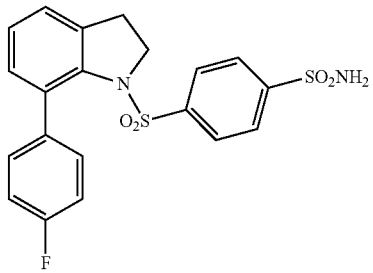

Compound 43

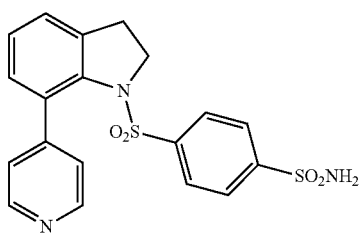

Compound 44

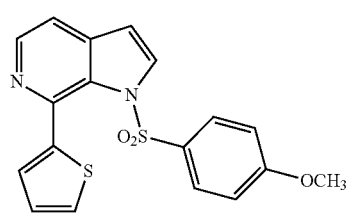

Compound 45

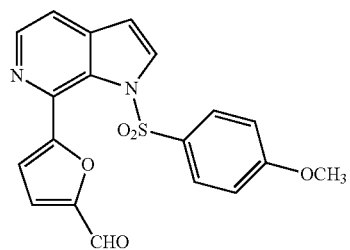

Compound 46

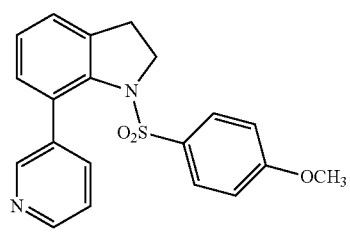

-continued

Compound 47

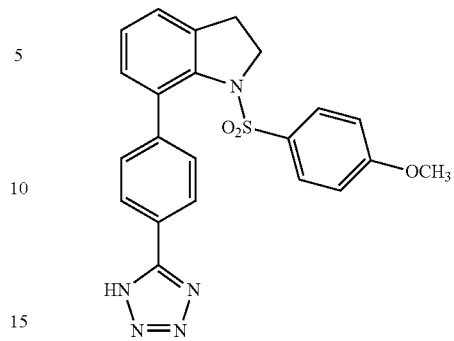

Compound 48

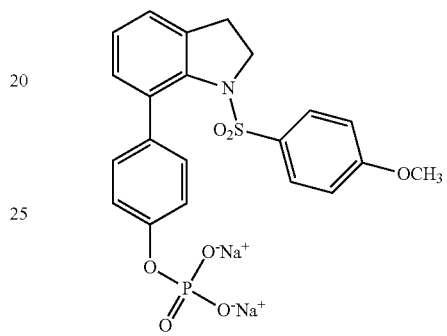

The aryl substituted sulfonamide compounds described herein can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The route shown in Scheme 1 below exemplifies synthesis of certain 7-aryl(heteroaryl) and 7-anilino-6-azaindole-1-sulfonamide compounds of the present invention. 2-Bromo-3-nitropyridine (1) reacts with vinylmagnesium bromide in THF, at −40-50° C. to afford 7-Bromo-6-azaindole (2), which reacts with 4-methoxyphenylsulfonyl chloride to provide 7-bromo-1-(4-methoxyphenylsulfonyl)-1H-pyrrolo[2,3-c]pyridine (3). The sulfonamide (3), is then either treated with a substituted or unsubstituted phenylboronic acid, Pd(PPh$_3$)$_4$, and K$_2$CO$_3$ in toluene/EtOH to afford final compound (4) or treated with a substituted or unsubstituted aniline in pyridine to yield final compound (5).

Scheme 1

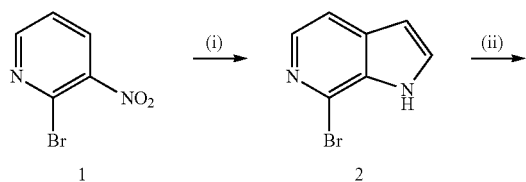

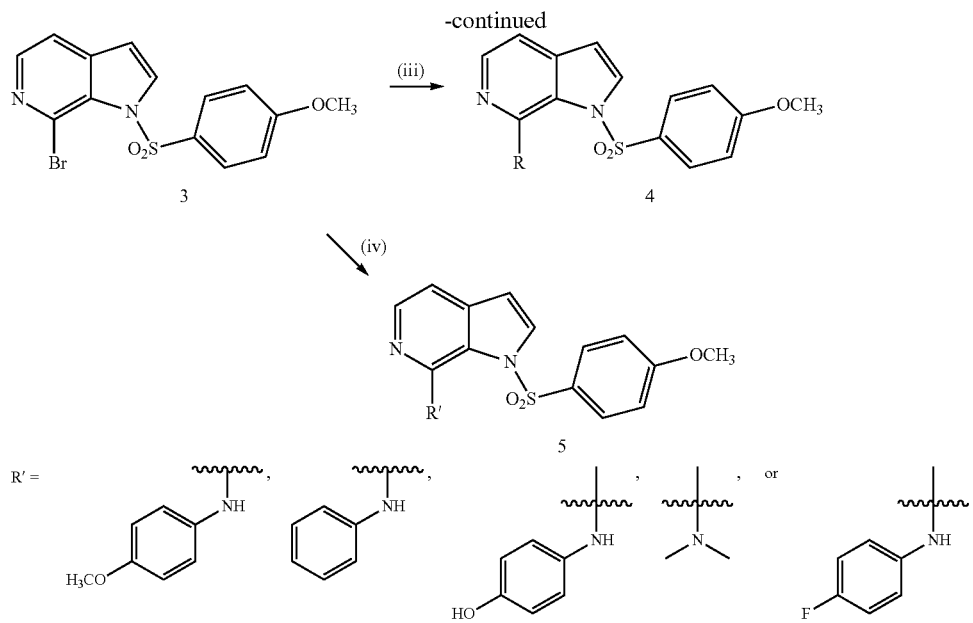

Reagents and conditions: (i) vinylmagnesium bromide, THF, −40-50° C.; (ii) 4-methoxyphenylsulfonyl chloride, Bu₄NHSO₄, KOH, CH₂Cl₂, rt; (iii) substituted or unsubstituted phenylboronic acid, Pd(PPh₃)₄, K₂CO₃, toluene/EtOH, reflux; (iv) substituted or unsubstituted aniline, pyridine, 110-120° C.

Similarly, the route shown in Scheme 2 below exemplifies synthesis of certain 7-aryl(heteroaryl)-indoline(indole)-1-sulfonamide compounds of the present invention. To synthesize indole-1-sulfonamide compound (9), 1-bromo-2-nitrobenzene (6) is reduced to afford 7-bromo-1H-indole (7), which reacts with 4-methoxyphenylsulfonyl chloride to provide 7-bromo-1-(4-methoxyphenylsulfonyl)-1H-indole (8). The sulfonamide (8), is then treated with an aryl or heteroaryl boronic acid, Pd(PPh₃)₄, and K₂CO₃ in toluene/EtOH to afford final compound (9). To synthesize indoline-1-sulfonamide compound (12), 7-bromo-1H-indole (7) is further reduced (with NaCNBH₃ and CH₃COOH, at room temperature) to afford 7-bromoindoline (10), which reacts with a substituted phenylsulfonyl chloride to provide bromo-indoline-sulfonamide (11). The bromo-indoline-sulfonamide (11) is then treated with an aryl or heteroaryl boronic acid, Pd(PPh₃)₄, and K₂CO₃ in toluene/EtOH to afford final compound (12), which can be further modified to obtain compound (13).

Scheme 2

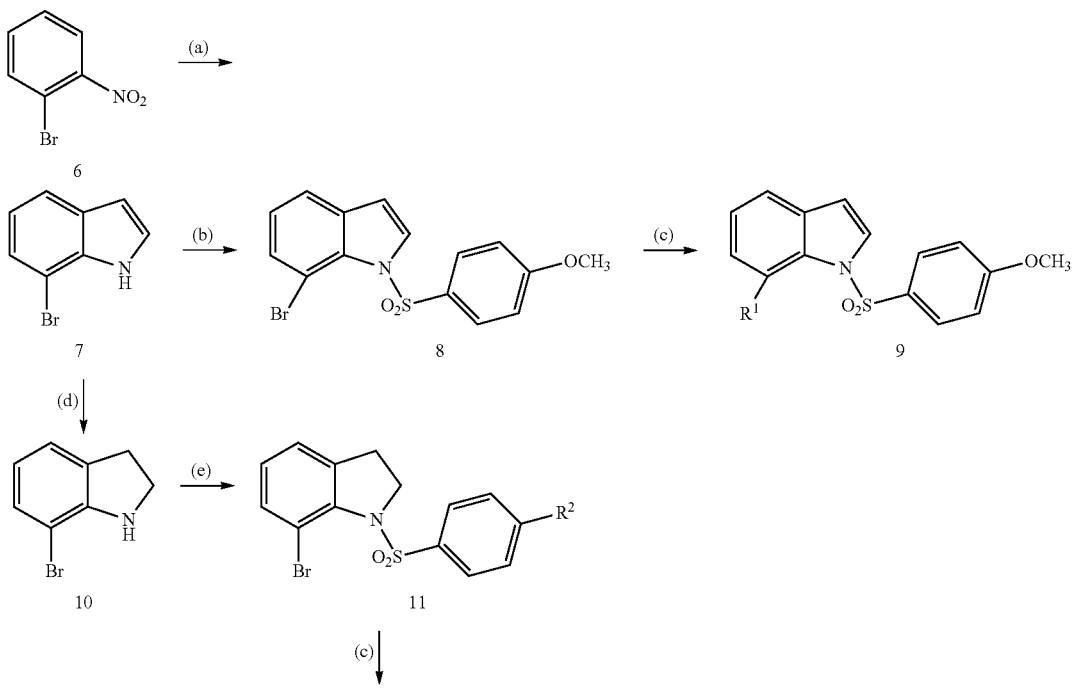

-continued

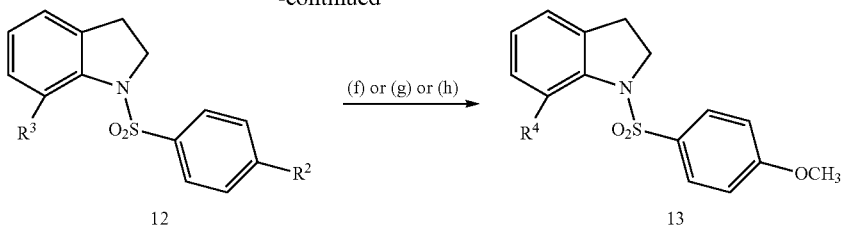

Reagents and conditions: (a) vinylmagnesium bromide, THF, −40-50° C.; (b) 4-methoxyphenylsulfonyl chloride, Bu₄NHSO₄, KOH, CH₂Cl₂, rt; (c) various aryl or heteroaryl boronic acid, Pd(PPh₃)₄, K₂CO₃, toluene/EtOH, reflux; (d) NaCNBH₃, CH₃COOH, rt; (e) 4-methoxyphenylsulfonyl chloride, pyridine, reflux; (f) Fe, NH₄Cl, isopropanol; (g) dimethylamine HCl, NaBH₃CN, Et₃N, EtOH; (h) first, CH₃OC(O)CH=PPh₃, THF; then, LiOH, MeOH, H₂O; next, O-(tetrahydro-2H-pyran-2-yl)hydroxylamine, PyBOP, Et₃N, DMF; last, 5% TFA, MeOH/CH₂Cl₂

Synthesis of the compounds of the present invention can also be achieved following the methods described in, e.g., *Tetrahedron lett.* 2008, 49, 5309, *J. Org. Chem.* 2001, 66, 638, *Tetrahedron* 1995, 51, 1167, and *J. Org. Chem.* 2002, 67, 2345, with necessary modifications as recognized by those skilled in the art.

An aryl substituted sulfonamide compound thus synthesized can be further purified by flash column chromatography, high performance liquid chromatography, crystallization, or any other suitable methods.

The aryl substituted sulfonamide compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention are (1) a pharmaceutical composition that contains an effective amount of at least one of the aryl substituted sulfonamide compounds of this invention and a pharmaceutically acceptable carrier, and (2) a method for treating cancer by administering to a subject in need of this treatment an effective amount of such an aryl substituted sulfonamide compound.

As used herein, the term "treating" refers to administering an aryl substituted sulfonamide compound to a subject that has cancer, or has a symptom of or a predisposition toward it, with the purpose to cure, heal, alleviate, relieve, alter, remedy, ameliorate, improve, affect, or reduce the risk of the disorder, the symptoms of or the predisposition toward the cancer. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

Cancer that can be treated by the methods of the invention includes both solid and haematological tumours of various organs. Examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An aryl substituted sulfonamide compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. One or more solubilizing agents (e.g., cyclodextrins) which form more soluble complexes with the active aryl substituted sulfonamide compounds can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the aryl substituted sulfonamide compounds in anticancer activities such as inhibiting growth of tumor cells. The compounds can further be examined for their efficacy in treating cancer. For example, a compound can be administered to an animal (e.g., a mouse model) having cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of [1-(4-methoxy-benzenesulfonyl)-1H-pyrrolo[2,3-c]pyridin-7-yl]-phenyl-amine (Compound 1)

7-Bromo-6-azaindole (2 in Scheme 1): A solution of 2-Bromo-3-nitropyridine (1 in Scheme 1, 2.0 g, 98%, 9.7 mmol) in dry THF (80 mL) was cooled to −78° C. Excess vinylmagnesium bromide (1.0 M in THF, 40 mL, 40 mmol) was added. The reaction mixture was stirred at −40~−50° C. for 1 h before it was quenched with saturated NaHCO$_3$ solution. The layers were separated and the aqueous layer was extracted with EtOAc (3 times). The combined organic layers were dried over MgSO$_4$, the dried solution was filtered, and the filtrate was concentrated. The residue was purified by flash chromatography (EtOAc:n-hexane=1:2) to afford 2 (1.1 g, 60%).

$^1$H NMR (500 MHz, CDCl$_3$): δ 6.66 (dd, 1H, J=2.9, 2.1 Hz), 7.43 (dd, 1H, J=2.9, 2.1 Hz), 7.51 (d, 1H, J=5.2 Hz), 8.03 (d, 1H, J=5.3 Hz), 8.79 (br, 1H).

7-Bromo-1-(4-methoxy-benzenesulfonyl)-1H-pyrrolo[2,3-c]pyridine (3 in Scheme 1): Potassium hydroxide (1.71 g, 30.45 mmol) and tetra-n-butylammonium hydrogen sulfate (0.345 g, 1.015 mmol) were added to a solution of 2 (2.0 g, 10.15 mmol) in dichloromethane (100 mL). The reaction mixture thus formed was stirred for 30 min. 4-Methoxysulfonyl chloride (4.2 g, 20.3 mmol) was added slowly to the reaction mixture. After 1 h the mixture was quenched with water and extracted with CH$_2$Cl$_2$. The combined organic layers were dried over MgSO$_4$, the dried solution was filtered, and the filtrate was concentrated. The residue was purified by silica gel column chromatography (EtOAc: n-hexane=1:1) to afford 3 (3.6 g, 97%).

$^1$H NMR (500 MHz, CDCl$_3$): δ 3.84 (s, 3H), 6.72 (d, 1H, J=3.7 Hz), 6.94 (d, 2H, J=8.9 Hz), 7.46 (d, 1H, J=5.1 Hz), 7.77 (d, 2H, J=8.9 Hz), 8.07 (d, 1H, J=3.7 Hz), 8.12 (d, 1H, J=5.2 Hz).

1-(4-Methoxy-benzenesulfonyl)-1H-pyrrolo[2,3-c]pyridin-7-yl]-phenyl-amine (Compound 1): A solution of 3 (0.2 g, 0.54 mmol) and aniline (0.2 mL, 2.17 mmol) in pyridine (1 mL) was heated in a sealed round bottle at 120-130° C. for 24 h. The solvent was removed and the residue was purified by flash chromatography (EtOAc:n-hexane=1:3) to give Compound 1 (78 mg, 38%).

Melting point ("mp"): 138.5-139.7° C.; $^1$H NMR (500 MHz, CDCl$_3$): δ 3.75 (s, 3H), 6.62 (d, 1H, J=3.5 Hz), 6.80 (d, 2H, J=8.9 Hz), 6.90 (d, 1H, J=5.5 Hz), 7.05 (t, 1H, J=7.4, 7.5 Hz), 7.36 (t, 2H, J=7.7, 8.0 Hz), 7.66 (d, 2H, J=8.9 Hz), 7.71 (d, 1H, J=3.7 Hz), 7.74 (d, 2H, J=7.7 Hz), 7.99 (d, 1H, J=5.3 Hz), 9.19 (s, 1H); $^{13}$C NMR (100 MHz, CDCl$_3$): δ 55.5, 108.0, 109.6, 114.5, 119.0, 119.2, 121.8, 128.4, 128.8, 129.0, 131.2, 139.6, 140.5, 141.1, 143.9, 163.7; MS (EI) m/z: 379.1 (M$^+$, 30%), 208.1 (100%); HRMS (EI) for C$_{20}$H$_{17}$N$_3$O$_3$S (M$^+$): calcd, 379.0990; found, 379.0990.

Example 2

Synthesis of 4-[1-(4-methoxy-benzenesulfonyl)-1H-pyrrolo[2,3-c]pyridin-7-ylamino]-phenol (Compound 2)

Compound 2 was prepared in a manner similar to that described in Example 1.

$^1$H NMR (500 MHz, CDCl$_3$): δ 3.78 (s, 3H), 6.62 (d, 1H, J=3.7 Hz), 6.72 (d, 2H, J=8.7 Hz), 6.84 (d, 2H, J=9.1 Hz), 6.85 (d, 1H, J=5.4 Hz), 7.30 (d, 2H, J=8.7 Hz), 7.68 (d, 2H, J=9.0 Hz), 7.72 (d, 1H, J=3.7 Hz), 7.89 (d, 1H, J=5.4 Hz), 8.85 (s, 1H); MS (EI) m/z: 395.2 (M$^+$, 37%), 224.1 (100%); HRMS (EI) for C$_{20}$H$_{17}$N$_3$O$_4$S (M$^+$): calcd, 395.0934; found, 395.0934.

Example 3

Synthesis of [1-(4-methoxy-benzenesulfonyl)-1H-pyrrolo[2,3-c]pyridin-7-yl]-dimethyl-amine (Compound 3)

Compound 3 was prepared in a manner similar to that described in Example 1.

Mp: 154.8-157.5° C.; $^1$H NMR (500 MHz, CDCl$_3$): δ 2.79 (s, 6H), 3.73 (s, 3H), 6.57 (d, 1H, J=3.7 Hz), 6.75 (d, 2H, J=8.9 Hz), 6.94 (d, 1H, J=5.2 Hz), 7.56 (d, 2H, J=8.9 Hz), 7.75 (d, 1H, J=3.7 Hz), 7.97 (d, 1H, J=5.2 Hz); MS (EI) m/z: 331.1 (M$^+$, 39%), 160.0 (100%); HRMS (EI) for C$_{16}$H$_{17}$N$_3$O$_3$S (M$^+$): calcd, 331.0996; found, 331.0996.

Example 4

Synthesis of [1-(4-methoxy-benzenesulfonyl)-1H-pyrrolo[2,3-c]pyridin-7-yl]-(4-methoxy-phenyl)-amine (Compound 4)

Compound 4 was prepared in a manner similar to that described in Example 1.

Mp: 155.5-158.3° C.; $^1$H NMR (500 MHz, CDCl$_3$): δ 3.78 (s, 3H), 3.83 (s, 3H), 6.62 (d, 1H, J=3.7 Hz), 6.83 (d, 2H, J=9.0 Hz), 6.85 (d, 1H, J=5.4 Hz), 6.94 (d, 2H, J=8.9 Hz), 7.58 (d, 2H, J=8.9 Hz), 7.68 (d, 2H, J=9.0 Hz), 7.70 (d, 1H, J=3.6 Hz), 7.94 (d, 1H, J=5.4 Hz), 9.03 (s, 1H); $^{13}$C NMR (125 MHz, CDCl$_3$): δ 55.5, 55.6, 107.4, 109.7, 114.2, 114.6, 118.8, 121.9, 128.6, 129.2, 131.2, 133.6, 139.6, 141.3, 144.6, 155.2, 163.8; MS (EI) m/z: 409.2 (M$^+$, 100%), 238.1 (81%); HRMS (EI) for C$_{21}$H$_{19}$N$_3$O$_4$S (M$^+$): calcd, 409.1097; found, 409.1098.

Example 5

Synthesis of (4-fluoro-phenyl)-[1-(4-methoxy-benzenesulfonyl)-1H-pyrrolo[2,3-c]pyridin-7-yl]-amine (Compound 5)

Compound 5 was prepared in a manner similar to that described in Example 1.

Mp: 125.1-127.1° C.; $^1$H NMR (500 MHz, CDCl$_3$): δ 3.74 (s, 3H), 6.62 (d, 1H, J=3.6 Hz), 6.80 (d, 2H, J=9.0 Hz), 6.89 (d, 1H, J=5.3 Hz), 7.05 (dd, 2H, J=8.7, 8.7 Hz), 7.65 (d, 2H, J=9.0 Hz), 7.69 (dd, 2H, J=9.0, 4.4 Hz), 7.69 (d, 1H, J=4.0 Hz), 7.95 (d, 1H, J=5.2 Hz), 9.14 (s, 1H); $^{13}$C NMR (100 MHz, CDCl$_3$): δ 55.6, 108.0, 109.7, 114.6, 115.3, 115.5, 118.9, 121.2, 128.5, 129.1, 131.3, 136.5, 139.7, 141.1, 144.0, 157.0, 159.4, 163.9; MS (EI) m/z: 397.1 (M$^+$, 58%), 226.1 (100%); HRMS (EI) for C$_{20}$H$_{16}$N$_3$O$_3$SF (M$^+$): calcd, 397.0895; found, 397.0895.

Example 6

Synthesis of 1-(4-methoxy-benzenesulfonyl)-7-phenyl-1H-pyrrolo[2,3-c]pyridine (Compound 6)

A solution of 3 (0.1 g, 0.273 mmol) in toluene (8 mL) was treated with tetrakis(triphenylphosphine) palladium (0.016 g, 0.014 mmol). An aqueous solution of $K_2CO_3$ (2 M, 1 mL) was then added, followed by a solution of phenylboronic acid (0.037 g, 0.3 mmol) in EtOH (5 mL). The resulting mixture was then refluxed for 24 h. The solvent was removed and the residue was purified by flash chromatography (EtOAc:n-hexane=2:3) to give Compound 6 (26.6 mg, 27%).

Mp: 148.9-151.0° C.; $^1$H NMR (500 MHz, CDCl$_3$): δ 3.79 (s, 3H), 6.73 (d, 2H, J=8.9 Hz), 6.76 (d, 1H, J=3.7 Hz), 7.18 (d, 2H, J=8.9 Hz), 7.37 (t, 3H, J=7.1, 7.5 Hz), 7.42 (d, 1H, J=5.1 Hz), 7.46 (d, 2H, J=6.9 Hz), 7.88 (d, 1H, J=3.7 Hz), 8.44 (d, 1H, J=5.3 Hz); MS (EI) m/z: 364.1 (M$^+$, 36%), 193.1 (100%); HRMS (EI) for $C_{20}H_{16}N_2O_3S$ (M$^+$): calcd, 364.0872; found, 364.0873.

Example 7

Synthesis of 4-[1-(4-methoxy-benzenesulfonyl)-1H-pyrrolo[2,3-c]pyridin-7-yl]-benzoic acid methyl ester (Compound 7)

Compound 7 was prepared in a manner similar to that described in Example 6.

Mp: 143.5-146.5° C.; $^1$H NMR (500 MHz, CDCl$_3$): δ 3.81 (s, 3H), 3.96 (s, 3H), 6.74 (d, 2H, J=8.9 Hz), 6.77 (d, 1H, J=3.7 Hz), 7.18 (d, 2H, J=8.9 Hz), 7.44 (d, 1H, J=5.2 Hz), 7.52 (d, 2H, J=8.3 Hz), 7.86 (d, 1H, J=3.7 Hz), 8.03 (d, 2H, J=8.2 Hz), 8.46 (d, 1H, J=5.1 Hz); MS (EI) m/z: 422.1 (M$^+$, 27%), 171.0 (100%); HRMS (EI) for $C_{22}H_{18}N_2O_5S$ (M$^+$): calcd, 422.0941; found, 422.0941.

Example 8

Synthesis of 7-(4-fluoro-phenyl)-1-(4-methoxy-benzenesulfonyl)-1H-pyrrolo[2,3-c]pyridine (Compound 8)

Compound 8 was prepared in a manner similar to that described in Example 6.

Mp: 136.0-137.0° C.; $^1$H NMR (500 MHz, CDCl$_3$): δ 3.80 (s, 3H), 6.75 (d, 2H, J=8.8 Hz), 6.75 (d, 1H, J=4.2 Hz), 7.03 (t, 2H, J=8.6, 8.7 Hz), 7.20 (d, 2H, J=8.9 Hz), 7.40 (d, 1H, J=5.1 Hz), 7.43 (ddd, 2H, J=8.3, 8.3, 2.7 Hz), 7.85 (d, 1H, J=3.7 Hz), 8.42 (d, 1H, J=5.1 Hz); $^{13}$C NMR (100 MHz, CDCl$_3$): δ 55.6, 108.9, 114.0, 114.4, 114.6, 128.8, 131.0, 134.1, 136.2, 139.8, 142.6, 147.2, 161.6, 163.6, 164.0; MS (EI) m/z: 382.1 (M$^+$, 63%), 211.1 (93%); HRMS (EI) for $C_{20}H_{15}N_2O_3SF$ (M$^+$): calcd, 382.0783; found, 382.0783.

Example 9

Synthesis of 7-(4-chloro-phenyl)-1-(4-methoxy-benzenesulfonyl)-1H-pyrrolo[2,3-c]pyridine (Compound 9)

Compound 9 was prepared in a manner similar to that described in Example 6.

Mp: 125.5-128.5° C.; $^1$H NMR (500 MHz, CDCl$_3$): δ 3.81 (s, 3H), 6.76 (d, 1H, J=3.8 Hz), 6.76 (d, 2H, J=8.8 Hz), 7.20 (d, 2H, J=9.0 Hz), 7.28 (d, 2H, J=8.5 Hz), 7.35 (d, 2H, J=8.5 Hz), 7.42 (d, 1H, J=5.3 Hz), 7.86 (d, 1H, J=3.8 Hz), 8.42 (d, 1H, J=5.1 Hz); $^{13}$C NMR (100 MHz, CDCl$_3$): δ 5.6, 108.8, 114.0, 114.9, 127.7, 128.7, 128.9, 130.6, 130.7, 134.1, 134.3, 138.4, 139.8, 142.5, 146.9, 163.6; MS (EI) m/z: 398.1 (M$^+$, 56%), 227.0 (42%), 171.0 (100%); HRMS (EI) for $C_{20}H_{15}N_2O_3SCl$ (M$^+$): calcd, 398.0499; found, 398.0499.

Example 10

Synthesis of 4-[1-(4-methoxy-benzenesulfonyl)-1H-pyrrolo[2,3-c]pyridin-7-yl]-phenol (Compound 10)

Compound 10 was prepared in a manner similar to that described in Example 6.

Mp: 179-182° C.; $^1$H NMR (500 MHz, CDCl$_3$): δ 3.68 (s, 3H), 6.62-6.65 (m, 5H), 7.04-7.07 (m, 4H), 7.29 (d, 1H, J=5.23 Hz), 7.78 (d, 1H, J=3.68 Hz), 8.14 (d, 1H, J=5.37 Hz); MS (EI) m/z: 380.0 (M$^+$, 32.5%), 209.0 (100.0%); HRMS (EI) for $C_{20}H_{16}N_2O_4S$ (M$^+$): calcd, 380.0830; found, 380.0824.

Example 11

Synthesis of 1-(4-methoxy-benzenesulfonyl)-7-(4-methoxy-phenyl)-1H-pyrrolo[2,3-c]pyridine (Compound 11)

Mp: 162.8-164.8° C.; $^1$H NMR (500 MHz, CDCl$_3$): δ 3.79 (s, 3H), 3.88 (s, 3H), 6.73 (d, 1H, J=3.8 Hz), 6.73 (d, 2H, J=8.9 Hz), 6.89 (d, 2H, J=8.7 Hz), 7.21 (d, 2H, J=9.0 Hz), 7.34 (d, 1H, J=5.2 Hz), 7.43 (d, 2H, J=8.7 Hz), 7.84 (d, 1H, J=3.7 Hz), 8.41 (d, 1H, J=5.1 Hz); $^{13}$C NMR (100 MHz, CDCl$_3$): δ 55.1, 55.5, 109.0, 112.9, 113.8, 114.0, 128.7, 128.8, 130.5, 130.9, 132.6, 134.0, 139.7, 142.6, 148.1, 159.6, 163.4; MS (EI) m/z: 394.1 (M$^+$, 25%), 223.1 (100%); HRMS (EI) for $C_{21}H_{18}N_2O_4S$ (M$^+$): calcd, 394.0990; found, 394.0991.

Example 12

Synthesis of {4-[1-(4-methoxy-benzenesulfonyl)-1H-pyrrolo[2,3-c]pyridin-7-yl]-phenyl}-dimethyl-amine (Compound 12)

Compound 12 was prepared in a manner similar to that described in Example 6.

Mp: 111.5-114.5° C.; $^1$H NMR (500 MHz, CDCl$_3$): δ 3.02 (s, 6H), 3.77 (s, 3H), 6.70 (d, 2H, J=9.2 Hz), 6.71 (d, 2H, J=8.7 Hz), 6.72 (d, 1H, J=3.8 Hz), 7.24 (d, 2H, J=8.8 Hz), 7.25 (d, 1H, J=5.1 Hz), 7.45 (d, 2H, J=8.7 Hz), 7.80 (d, 1H, J=3.6 Hz), 8.38 (d, 1H, J=5.1 Hz); MS (EI) m/z: 407.2 (M$^+$, 20%), 236.1 (100%); HRMS (EI) for $C_{22}H_{21}N_3O_3S$ (M$^+$): calcd, 407.1305; found, 407.1305.

Example 13

Synthesis of 1-(4-methoxy-benzenesulfonyl)-7-pyridin-4-yl-1H-pyrrolo[2,3-c]pyridine (Compound 13)

Compound 13 was prepared in a manner similar to that described in Example 6.

Mp: 193.1-194.3° C.; $^1$H NMR (500 MHz, CDCl$_3$): δ 3.81 (s, 3H), 6.72-6.79 (m, 3H), 7.19 (d, 2H, J=8.93 Hz), 7.32~7.33 (m, 2H), 7.48 (dd, 1H, J=4.49 Hz), 7.87 (d, 1H, J=3.62 Hz), 8.46 (d, 1H, J=5.12 Hz), 8.60 (d, 2H, J=5.93 Hz). MS (EI) m/z: 365.0 (M$^+$, 100.0%); HRMS (EI) for $C_{19}H_{15}N_3O_3S$ (M$^+$): calcd, 365.0834; found, 365.0836.

Example 14

Synthesis of 1-(4-methoxy-benzenesulfonyl)-7-(4-nitro-phenyl)-1H-pyrrolo[2,3-c]pyridine (Compound 14)

Compound 14 was prepared in a manner similar to that described in Example 6.

Mp: 177.5-178.8° C.; $^1$H NMR (500 MHz, CDCl$_3$): δ 3.82 (s, 3H), 6.76 (d, 2H, J=8.91 Hz), 7.79 (d, 1H, J=3.685 Hz), 7.20 (d, 2H, J=8.69 Hz), 7.47 (d, 1H, J=5.11 Hz), 7.64 (d, 2H, J=8.67 Hz), 7.83 (d, 1H, J=3.71 Hz), 8.21 (d, 2H, J=8.62 Hz), 8.48 (d, 1H, J=5.08 Hz); MS (EI) m/z: 409.0 (M$^+$, 32.0%), 171.0 (100.0%); HRMS (EI) for C$_{20}$H$_{15}$N$_3$O$_5$S (M$^+$): calcd, 409.0732; found, 409.0730.

Example 15

Synthesis of 1-(4-methoxy-benzenesulfonyl)-7-(4-trifluoromethyl-phenyl)-1H-pyrrolo[2,3-c]pyridine (Compound 15)

Compound 15 was prepared in a manner similar to that described in Example 6.
Mp: 143.1-144.9° C.; $^1$H NMR (500 MHz, CDCl$_3$): δ 3.81 (s, 3H), 6.74 (d, J=8.8 Hz, 2H), 6.78 (d, J=3.6 Hz, 1H), 7.16 (d, J=8.8 Hz, 2H), 7.47 (d, J=5.2 Hz, 1H), 7.49 (d, J=8.0 Hz, 2H), 7.56 (d, J=8.0 Hz, 2H), 7.88 (d, J=3.6 Hz, 1H), 8.45 (d, J=5.1 Hz, 1H).

Example 16

Synthesis of 7-furan-2-yl-1-(4-methoxy-benzenesulfonyl)-1H-pyrrolo[2,3-c]pyridine (Compound 16)

Compound 16 was prepared in a manner similar to that described in Example 6.
Mp: 127.1-130.3° C.; $^1$H NMR (500 MHz, CDCl$_3$): δ 3.79 (s, 3H), 6.56 (q, 1H, J=2.36 Hz), 6.70 (d, 1H, J=3.70 Hz), 6.80 (d, 2H, J=8.94 Hz), 6.83 (d, 1H, J=3.315 Hz), 7.36 (d, 1H, J=5.14 Hz), 7.42 (d, 2H, J=9.02 Hz), 7.47 (s, 1H), 7.74 (d, 1H, J=3.71 Hz), 8.43 (d, 1H, J=5.08 Hz); MS (EI) m/z: 354.1 (M$^+$, 17.0%), 184.1 (100.0%); HRMS (EI) for C$_{18}$H$_{14}$N$_2$O$_4$S (M$^+$): calcd, 354.0674; found, 354.0676.

Example 17

Synthesis of 4-[1-(4-methoxy-benzenesulfonyl)-2,3-dihydro-1H-indol-7-yl]-benzonitrile (Compound 17)

7-Bromo-1-(4-methoxy-benzenesulfonyl)-2,3-dihydro-1H-indole (11 in scheme 2 wherein R$_2$=OCH$_3$): A solution of 7-bromo-1H-indole (0.30 g, 1.53 mmol) in glacial acetic acid (1.5 mL) was treated with sodium cyanoborohydride (0.14 g, 2.29 mmol) under N$_2$ at 0° C. After aqueous sodium hydroxide solution was added to quench excess acid, the resulting mixture was then extracted with CH$_2$Cl$_2$ (20 mL×3). The combined organic layers were dried over MgSO$_4$, the dried solution was filtered, and the filtrate was concentrated. The residue was dissolved in pyridine and 4-methoxyphenylsulfonyl chloride was added. The reaction mixture was refluxed overnight. The solvent was removed and the residue was purified by flash chromatography (EtOAc: n-hexane=1:2) to afford 11 (370.6 mg, 87%).
$^1$H NMR (500 MHz, CDCl$_3$): δ 2.40 (t, 2H, J=7.22 Hz), 3.85 (s, 3H), 3.97 (t, 2H, J=7.25 Hz), 6.88 (d, 2H, J=8.9 Hz), 6.99 (t, 1H, J=7.59 Hz), 7.04 (d, 1H, J=7.02 Hz), 7.46 (d, 1H, J=7.72 Hz), 7.60 (d, 2H, J=8.89 Hz).
4-[1-(4-Methoxy-benzenesulfonyl)-2,3-dihydro-1H-indol-7-yl]-benzonitrile: A solution of 11 (0.15 g, 0.40 mmol) in toluene (10 mL) was treated with tetrakis(triphenylphosphine) palladium (0.02 g, 0.02 mmol) under N$_2$. An aqueous solution of K$_2$CO$_3$ (2 M, 1.4 mL) was then added, followed by a solution of 4-cyanophenylboronic acid (0.24 g, 1.63 mmol) in EtOH (8 mL). The resulting mixture was refluxed for 24 h. The solvent was removed and the residue was purified by flash chromatography (EtOAc:n-hexane=1:3) to afford Compound 17 (50.0 mg, 31%).
Mp: 157.2-158.9° C.; $^1$H NMR (500 MHz, CDCl$_3$): δ 2.34 (t, J=7.4 Hz, 2H), 3.83 (s, 3H), 4.03 (t, J=7.3 Hz, 2H), 6.79 (d, J=8.8 Hz, 2H), 7.11 (d, J=6.9 Hz, 1H), 7.24-7.31 (m, 4H), 7.70 (d, J=8.3 Hz, 2H), 7.78 (d, J=8.3 Hz, 2H); MS (EI) m/z: 390 (M$^+$, 100%); HRMS (EI) calcd for C$_{22}$H$_{18}$O$_3$N$_2$S$_1$ (M$^+$): 390.1038; found 390.1040.

Example 18

Synthesis of 4-[1-(4-methoxy-benzenesulfonyl)-1H-indol-7-yl]-benzonitrile (Compound 18)

Compound 18 was prepared in a manner similar to that described in Example 17.
Mp: 164.3-165.7° C.; $^1$H NMR (500 MHz, CDCl$_3$): δ 3.79 (s, 3H), 6.74-6.76 (m, 3H), 7.03 (d, 1H, J=7.45 Hz), 7.19 (d, 2H, J=8.86 Hz), 7.28 (d, 1H, J=7.59 Hz), 7.40 (d, 2H, J=8.07 Hz), 7.53 (d, 1H, J=7.87 Hz), 7.58 (d, 2H, J=8.16 Hz), 7.65 (d, 1H, J=3.73 Hz).

Example 19

Synthesis of 7-(4-fluoro-phenyl)-1-(4-methoxy-benzenesulfonyl)-1H-indole (Compound 19)

Compound 19 was prepared in a manner similar to that described in Example 17.
Mp: 181.2-182.4° C.; $^1$H NMR (500 MHz, CDCl$_3$): δ 3.79 (s, 3H), 6.73-6.74 (m, 3H), 6.95 (t, 2H, J=8.63 Hz), 7.01 (d, 1H, J=7.32 Hz), 7.18~7.24 (m, 5H), 7.49 (d, 1H, J=7.72 Hz), 7.70 (d, 1H, J=3.63 Hz); $^{13}$C NMR (100 MHz, CDCl$_3$): δ55.6, 110.0, 113.8, 114.1, 120.6, 123.7, 128.6, 129.7, 129.8, 130.8, 131.0, 133.4, 133.5, 136.6, 136.7, 160.8, 163.2, 163.3; MS (EI) m/z: 381.0 (M$^+$, 93.1%), 210.0 (100.0%).

Example 20

Synthesis of 4-[1-(4-methoxy-benzenesulfonyl)-2,3-dihydro-1H-indol-7-yl]-phenylamine (Compound 20)

Compound 20 was prepared in a manner similar to that described in Example 17.
Mp: 183.9-185.6° C.; $^1$H NMR (500 MHz, CDCl$_3$): δ 2.30 (t, J=7.3 Hz, 2H), 3.81 (s, 3H), 4.01 (t, J=7.4 Hz, 2H), 6.73-6.78 (m, 4H), 6.96 (d, J=6.9 Hz, 1H), 7.17 (t, J=7.5 Hz, 1H), 7.26-7.28 (m, 1H), 7.34-7.35 (m, 2H), 7.50-7.51 (m, 2H).

Example 21

Synthesis of 7-(3,4-difluoro-phenyl)-1-(4-methoxy-benzenesulfonyl)-2,3-dihydro-1H-indole (Compound 21)

Compound 21 was prepared in a manner similar to that described in Example 17.
Mp: 180.2-181.4° C.; $^1$H NMR (500 MHz, CDCl$_3$): δ 2.33 (t, 2H, J=7.37 Hz), 3.82 (s, 3H), 4.02 (t, 2H, J=7.38 Hz), 6.79 (d, 2H, J=8.85 Hz), 7.06 (bd, 1H, J=7.03 Hz), 7.15~7.24 (m, 3H), 7.32 (d, 2H, J=8.81 Hz), 7.37~7.40 (m, 1H), 7.44-7.48 (m, 1H); $^{13}$C NMR (125 MHz, CDCl$_3$): δ 52.0, 55.5, 113.8, 116.9, 117.1, 117.3, 124.1, 124.2, 124.3, 127.3, 128.9, 129.2, 129.5, 133.6, 137.4, 138.5, 140.0, 148.2, 148.3, 148.8, 149.0, 150.6, 150.8, 151.3, 151.4, 163.2; MS (EI) m/z: 400.9 (M$^+$, 2.0%), 230.2 (100%); HRMS (EI) for $C_{21}H_{17}F_2NO_3S$ (M$^+$): calcd, 401.089; found, 401.0905.

Example 22

Synthesis of 1-(4-methoxy-benzenesulfonyl)-7-pentafluorophenyl-2,3-dihydro-1H-indole (Compound 22)

Compound 22 was prepared in a manner similar to that described in Example 17.

Mp: 108.1-109.2° C.; $^1$HNMR (500 MHz, CDCl$_3$): δ 2.87 (t, J=8.4 Hz, 2H), 3.80 (s, 3H), 3.89 (t, J=8.4 Hz, 2H), 6.88 (d, J=8.8 Hz, 2H), 6.96 (t, J=7.4 Hz, 1H), 7.06 (d, J=7.3 Hz, 1H), 7.18 (t, J=7.7 Hz, 1H), 7.63 (d, J=8.1 Hz, 1H), 7.71 (d, J=8.9 Hz, 2H).

Example 23

Synthesis of 1-(4-methoxy-benzenesulfonyl)-7-(4-methoxy-phenyl)-2,3-dihydro-1H-indole (Compound 23)

Compound 23 was prepared in a manner similar to that described in Example 17.

Mp: 176.3-177.4° C.; $^1$H NMR (500 MHz, CDCl$_3$): δ 2.32 (t, 2H, J=7.31 Hz), 3.81 (s, 3H), 3.84 (s, 3H), 4.02 (t, 2H, J=7.34 Hz), 6.77 (d, 2H, J=8.92 Hz), 6.95 (d, 2H, J=8.72 Hz), 6.99 (d, 1H, J=7.50 Hz,), 7.18 (t, 1H, J=7.52 Hz), 7.27 (d, 1H, J=7.59 Hz), 7.32 (d, 2H, J=8.9 Hz), 7.61 (d, 2H, J=8.69 Hz); $^{13}$C NMR (100 MHz, CDCl$_3$): δ 51.0, 55.1, 55.5, 113.6, 123.0, 127.1, 129.2, 129.3, 129.5, 132.9, 135.4, 138.2, 139.9, 158.5, 163.1; MS (EI) m/z: 395.0 (M$^+$, 15.0%), 224.2 (100.0%); HRMS (EI) for $C_{22}H_{21}NO_4S$ (M$^+$): calcd, 395.1191; found, 395.1185.

Example 24

Synthesis of 1-(4-methoxy-benzenesulfonyl)-7-pyridin-4-yl-2,3-dihydro-1H-indole (Compound 24)

Compound 24 was prepared in a manner similar to that described in Example 17.

Mp: 195.9-196.8° C.; $^1$H NMR (500 MHz, CDCl$_3$): δ 2.19 (t, 2H, J=7.39 Hz), 3.80 (s, 3H), 3.92 (t, 2H, J=7.45 Hz), 6.70 (d, 2H, J=8.91 Hz), 7.03 (d, 1H, J=7.06 Hz), 7.15~7.22 (m, 4H), 7.55 (dd, 2H, J=4.58 Hz), 8.44 (dd, 2H, J=4.83 Hz); MS (EI) m/z: 366.1 (M$^+$, 34.1%), 195.1 (100.0%); HRMS (EI) for $C_{20}H_{18}N_2O_3S$ (M$^+$): calcd, 366.1038; found, 366.1041.

Example 25

Synthesis of 7-(6-fluoro-pyridin-3-yl)-1-(4-methoxy-benzenesulfonyl)-2,3-dihydro-1H-indole (Compound 25)

Compound 25 was prepared in a manner similar to that described in Example 17.

Mp: 139.8-141.7° C.; $^1$H NMR (500 MHz, CDCl$_3$): δ 2.36 (t, J=7.3 Hz, 2H), 3.82 (s, 3H), 4.03 (t, J=7.4 Hz, 2H), 6.80 (d, J=8.7 Hz, 2H), 6.97 (dd, J=8.4, 2.7 Hz, 1H), 7.11 (d, J=6.7 Hz, 1H), 7.23-7.28 (m, 3H), 7.32 (d, J=8.8 Hz, 2H), 8.08-8.12 (m, 1H), 8.45 (m, 1H).

Example 26

Synthesis of 4-[1-(4-methoxy-benzenesulfonyl)-2,3-dihydro-1H-indol-7-yl]-phenol (Compound 26)

Compound 26 was prepared in a manner similar to that described in Example 17.

Mp: 179.4-180.5° C.; $^1$H NMR (500 MHz, CDCl$_3$): δ 2.29 (t, 2H, J=7.27 Hz), 3.80 (s, 3H), 4.02 (t, 2H, J=7.31 Hz), 6.79 (d, 2H, J=8.83 Hz), 6.82 (d, 2H, J=8.53 Hz), 6.98 (d, 1H, J=7.44 Hz), 7.18 (t, 1H, J=7.54 Hz), 7.28 (d, 1H, J=7.61 Hz), 7.34 (d, 2H, J=8.82 Hz), 7.55 (d, 2H, J=8.59 Hz); $^{13}$C NMR (100 MHz, CDCl$_3$): δ 51.9, 55.5, 77.2, 113.8, 115.3, 123.0, 127.2, 129.0, 129.4, 129.6, 135.5, 138.2, 139.8, 154.8, 163.1; MS (EI) m/z: 381.1 (M$^+$, 7.0%), 210.2 (100.0%); HRMS (EI) for $C_{21}H_{19}NO_4S$ (M$^+$): calcd, 381.1034; found, 381.1033.

Example 27

Synthesis of 1-(4-methoxy-benzenesulfonyl)-7-phenyl-2,3-dihydro-1H-indole (Compound 27)

Compound 27 was prepared in a manner similar to that described in Example 17.

Mp: 165.9-167.8° C.; $^1$H NMR (500 MHz, CDCl$_3$): δ 2.00 (t, 2H, J=7.32 Hz), 3.52 (s, 3H), 3.68 (t, 2H, J=7.42 Hz), 6.50 (d, 2H, J=8.83 Hz), 6.73 (d, 1H, J=7.06 Hz), 6.88~6.96 (m, 4H), 7.30 (d, 2H, J=7.55 Hz); MS (EI) m/z: 433.0 (M$^+$, 5.7%), 194.0 (100.0%); HRMS (EI) for $C_{22}H_{18}F_3NO_3S$ (M$^+$): calcd, 433.0959; found, 433.0956.

Example 28

Synthesis of 7-(4-fluoro-phenyl)-1-(4-methoxy-benzenesulfonyl)-2,3-dihydro-1H-indole (Compound 28)

Compound 28 was prepared in a manner similar to that described in Example 17.

Mp: 178.1-179.4° C.; $^1$H NMR (500 MHz, CDCl$_3$): δ 2.33 (t, 2H, J=7.33 Hz), 3.82 (s, 3H), 4.02 (t, 2H, J=7.38 Hz), 6.78 (d, 2H, J=8.77 Hz), 7.04 (d, 1H, J=7.30 Hz), 7.10 (t, 2H, J=8.66 Hz), 7.21 (t, 1H, J=7.50 Hz, H-5), 7.27 (d, 1H, J=7.89 Hz, H-6), 7.32 (d, 2H, J=8.77 Hz, H-2", 6"), 7.63 (d, 2H, J=7.95 Hz, H-2',6'); MS (EI) m/z: 383.0 (M$^+$, 16.6%), 212.0 (100.0%); HRMS (EI) for $C_{21}H_{18}FNO_3S$ (M$^+$): calcd, 383.0991; found, 383.0922.

Example 29

Synthesis of 7-furan-2-yl-1-(4-methoxy-benzenesulfonyl)-2,3-dihydro-1H-indole (Compound 29)

Compound 29 was prepared in a manner similar to that described in Example 17.

Mp: 176.7-177.7° C.; $^1$H NMR (500 MHz, CDCl$_3$): δ 2.16 (t, 2H, J=7.33 Hz), 3.83 (s, 3H), 4.00 (t, 2H, J=7.40 Hz), 6.51 (q, 1H, J=1.71 Hz), 6.81 (d, 2H, J=8.86 Hz), 6.95 (d, 1H, J=7.57 Hz), 6.98 (d, 1H, J=3.28 Hz), 7.19 (t, 1H, J=7.61 Hz), 7.39 (d, 2H, J=8.90 Hz), 7.51 (d, 1H, J=1.12 Hz), 7.60 (d, 1H, J=8.12 Hz); MS (EI) m/z: 355.0 (M$^+$, 15.7%), 184.0 (100.0%); HRMS (EI) for $C_{19}H_{17}NO_4S$ (M$^+$): calcd, 355.0878; found, 355.0881.

Example 30

Synthesis of 1-(4-methoxy-benzenesulfonyl)-7-thiophen-2-yl-2,3-dihydro-1H-indole (Compound 30)

Compound 30 was prepared in a manner similar to that described in Example 17.

Mp: 127.7-129.1° C.; $^1$H NMR (500 MHz, CDCl$_3$): δ 2.40 (t, 2H, J=7.23 Hz), 3.85 (s, 3H), 3.98 (t, 2H, J=7.21 Hz), 6.80 (d, 1H, J=8.85 Hz), 6.87 (d, 2H, J=8.85 Hz), 6.89-7.05 (m, 3H), 7.46-7.60 (m, 2H), 7.60 (d, 2H, J=8.85 Hz); MS (EI) m/z: 371.0 (M$^+$, 15.7%), 200.0 (100.0%); HRMS (EI) for C$_{19}$H$_{17}$NO$_3$S$_2$(M$^+$): calcd, 371.0649; found, 371.0657.

Example 31

Synthesis of {4-[1-(4-methoxy-benzenesulfonyl)-2,3-dihydro-1H-indol-7-yl]-phenyl}-dimethyl-amine (Compound 31)

Compound 31 was prepared in a manner similar to that described in Example 17.

Mp: 178.4-179.7° C.; $^1$H NMR (500 MHz, CDCl$_3$): δ 2.30 (t, 2H, J=7.30 Hz), 2.99 (s, 6H), 3.81 (s, 3H), 4.02 (t, 2H, J=7.34 Hz), 6.75~6.78 (m, 4H), 6.94 (d, 1H, J=7.18 Hz), 7.16 (t, 1H, J=7.53 Hz), 7.29 (d, 1H, J=7.71 Hz), 7.34 (d, 2H, J=8.77 Hz), 7.59 (d, 2H, J=8.74 Hz); MS (EI) m/z: 408.1 (M$^+$, 20.6%), 237.1 (100.0%); HRMS (EI) for C$_{23}$H$_{24}$N$_2$O$_3$S (M$^+$): calcd, 408.1507; found, 408.1511.

Example 32

Synthesis of 1-(4-methoxy-benzenesulfonyl)-7-(3,4,5-trimethoxy-phenyl)-2,3-dihydro-1H-indole (Compound 32)

Compound 32 was prepared in a manner similar to that described in Example 17.

Mp: 202.5-204.8° C.; $^1$H NMR (500 MHz, CDCl$_3$): δ 2.21 (t, 2H, J=7.28 Hz), 3.65 (s, 3H), 3.68 (s, 3H), 3.70 (s, 6H,), 3.85 (t, 2H, J=7.33 Hz), 6.64 (bd, 2H, J=8.85 Hz), 6.71 (s, 2H), 6.89 (d, 1H, J=7.22 Hz), 7.04 (t, 1H, J=7.49 Hz), 7.12~7.14 (m, 3H); MS (EI) m/z: 455.0 (M$^+$, 36.3%), 253.0 (100.0%); HRMS (EI) for C$_{24}$H$_{25}$NO$_6$S (M$^+$): calcd, 455.1402; found, 455.1410.

Example 33

Synthesis of 7-(4-chloro-phenyl)-1-(4-methoxy-benzenesulfonyl)-2,3-dihydro-1H-indole (Compound 33)

Compound 33 was prepared in a manner similar to that described in Example 17.

Mp: 177.1-178.3° C.; $^1$H NMR (500 MHz, CDCl$_3$): δ 2.35 (t, 2H, J=7.34 Hz), 3.82 (s, 3H), 4.03 (t, 2H, J=7.41 Hz), 6.78 (d, 2H, J=8.86 Hz), 7.06 (bd, 1H, J=6.98 Hz), 7.21 (t, 1H, J=7.49 Hz), 7.26 (bd, 1H, J=6.95 Hz), 7.31 (d, 2H, J=8.83 Hz), 7.37 (d, 2H, J=8.37 Hz), 7.59 (d, 2H, J=8.45 Hz); MS (EI) m/z: 399.0 (M$^+$, 26.5%), 228.0 (100.0%); HRMS (EI) for C$_{21}$H$_{18}$ClNO$_3$S (M$^+$): calcd, 399.0695; found, 399.0703.

Example 34

Synthesis of 1-(4-methoxy-benzenesulfonyl)-7-(4-trifluoromethyl-phenyl)-2,3-dihydro-1H-indole (Compound 34)

Compound 34 was prepared in a manner similar to that described in Example 17.

Mp: 179.7-181.0° C.; $^1$H NMR (500 MHz, CDCl$_3$): δ 2.37 (t, 2H, J=7.39 Hz), 3.82 (s, 3H), 4.05 (t, 2H, J=7.36 Hz), 6.78 (d, 2H, J=8.83 Hz), 7.10 (d, 1H, J=7.02 Hz), 7.23~7.31 (m, 4H), 7.65 (d, 2H, J=8.22 Hz), 7.76 (d, 2H, J=8.17 Hz); MS (EI) m/z: 433.0 (M$^+$, 5.7%), 194.0 (100.0%); HRMS (EI) for C$_{22}$H$_{18}$F$_3$NO$_3$S (M$^+$): calcd, 433.0959; found, 433.0956.

Example 35

Synthesis of 7-(3-fluoro-phenyl)-1-(4-methoxy-benzenesulfonyl)-2,3-dihydro-1H-indole (Compound 35)

Compound 35 was prepared in a manner similar to that described in Example 17.

Mp: 180.0-181.3° C.; $^1$H NMR (500 MHz, CDCl$_3$): δ 2.35 (t, 2H, J=7.36 Hz), 3.82 (s, 3H), 4.02 (t, 2H, J=7.36 Hz), 6.79 (d, 2H, J=8.82 Hz), 6.06~6.07 (m, 2H), 7.22 (d, 1H, J=7.50 Hz), 7.28~7.39 (m, 5H), 7.46 (d, 1H, J=7.69 Hz); MS (EI) m/z: 383.0 (M$^+$, 20.6%), 228.0 (100.0%); HRMS (EI) for C$_{21}$H$_{18}$ClNO$_3$S (M+): calcd, 399.0695; found, 399.0703.

Example 36

Synthesis of 1-(4-methoxy-benzenesulfonyl)-7-pyridin-2-yl-2,3-dihydro-1H-indole (Compound 36)

Compound 36 was prepared in a manner similar to that described in Example 17.

Mp: 195.1-197° C.; $^1$HNMR (500 MHz, CDCl$_3$): δ 2.22 (t, J=7.3 Hz, 2H), 3.71 (s, 3H), 3.92 (t, J=7.4 Hz, 2H), 6.71 (d, J=8.8 Hz, 2H), 7.01 (d, J=6.6 Hz, 1H), 7.15-7.20 (m, 4H), 7.29-7.32 (m, 1H), 7.93-7.96 (m, 1H), 8.36 (dd, J=4.6, 1.2 Hz, 1H), 8.70 (d, J=1.8 Hz, 1H); MS (EI) m/z 366 (M$^+$, 40%), 195 (100%); HRMS (EI) calcd for C$_{20}$H$_{18}$O$_3$N$_2$S$_1$ (M+), 366.1038; found 366.1036.

Example 37

Synthesis of 1-(4-methoxy-benzenesulfonyl)-7-(4-nitro-phenyl)-2,3-dihydro-1H-indole (Compound 37)

Compound 37 was prepared in a manner similar to that described in Example 17.

Mp: 177.1-178.4° C.; $^1$H NMR (500 MHz, CDCl$_3$): δ 2.34 (t, 2H, J=7.40 Hz), 3.82 (s, 3H), 4.05 (t, 2H, J=7.47 Hz), 6.80 (d, 2H, J=8.98 Hz), 7.14 (d, 1H, J=7.07 Hz), 7.27~7.33 (m, 4H), 7.82~7.84 (m, 2H), 8.27~8.29 (m, 2H); MS (EI) m/z: 410.0 (M$^+$, 5.2%), 237.1 (100.0%); HRMS (EI) for C$_{21}$H$_{18}$N$_2$O$_5$S (M$^+$): calcd, 410.0936; found, 410.0944.

Example 38

Synthesis of 4-[1-(4-methoxy-benzenesulfonyl)-2,3-dihydro-1H-indol-7-yl]-benzaldehyde (Compound 38)

Compound 38 was prepared in a manner similar to that described in Example 17.

Mp: 152-153° C.; ¹HNMR (500 MHz, CDCl₃): δ 2.34 (t, J=7.3 Hz, 2H), 3.82 (s, 3H), 4.04 (t, J=7.4 Hz, 2H), 7.10 (d, J=7.3 Hz, 1H), 7.24-7.27 (m, 2H), 7.30-7.34 (m, 3H), 7.85 (d, J=8.0 Hz, 2H), 7.94 (d, J=8.0 Hz, 2H).

Example 39

Synthesis of {4-[1-(4-methoxy-benzenesulfonyl)-2,3-dihydro-1H-indol-7-yl]-benzyl}-dimethyl-amine (Compound 39)

Compound 39 was prepared in a manner similar to that described in Example 17.
Mp: 165-166° C.; ¹H NMR (500 MHz, CDCl₃): δ 2.32 (m, 2H), 2.23 (s, 6H), 3.57 (s, 2H), 3.81 (s, 3H), 4.02 (t, J=7.3 Hz, 2H), 6.78 (d, J=8.7 Hz, 2H), 7.03 (d, J=7.2 Hz, 1H), 7.21 (t, J=7.4 Hz, 1H), 7.31-7.33 (m, 3H), 7.38 (d, J=7.9 Hz, 2H), 7.65 (d, J=7.9 Hz, 2H).

Example 40

Synthesis of 4-[1-(4-methoxy-benzenesulfonyl)-2,3-dihydro-1H-indol-7-yl]-benzoic acid (Compound 40)

Compound 40 was prepared in a manner similar to that described in Example 17.
Mp: 130.3-132.1° C.; ¹HNMR (500 MHz, CD₃OD): δ 2.21 (t, J=7.3 Hz, 2H), 3.70 (s, 3H), 3.89-3.99 (m, 2H), 6.68 (d, J=8.7 Hz, 2H), 6.97 (d, J=7.2 HZ, 1H), 7.11-7.20 (m, 3H), 7.61 (d, J=8.2 Hz, 2H), 7.90 (d, J=7.3 Hz, 1H), 7.96 (d, J=8.2 Hz, 2H).

Example 41

Synthesis of N-hydroxy-3-{4-[1-(4-methoxy-benzenesulfonyl)-2,3-dihydro-1H-indol-7-yl]-phenyl}-acrylamide (Compound 41)

Compound 41 was prepared in a manner similar to that described in Example 17.
Mp: 200-201° C.; ¹H NMR (500 MHz, CDCl₃) δ 2.20 (t, J=7.2 Hz, 2H), 3.70 (s, 3H) 3.91 (t, J=7.3 Hz, 2H), 6.30 (br, 1H), 6.68 (d, J=8.8 Hz, 2H), 6.95 (d, J=7.1 Hz, 1H), 7.12 (1H, J=7.5 Hz, 1H), 7.17-7.20 (m, 3H), 7.43-7.57 (m, 5H).

Example 42

Synthesis of 4-[7-(4-fluoro-phenyl)-2,3-dihydro-indole-1-sulfonyl]-benzenesulfonamide (Compound 42)

Compound 42 was prepared in a manner similar to that described in Example 17.
Mp: 188.7-190.2° C.; ¹H NMR (500 MHz, CDCl₃): δ 2.28 (t, 2H, J=7.3 Hz), 3.97 (t, 2H, J=7.3 Hz), 6.93~6.97 (m, 3H), 7.10~7.16 (m, 2H), 7.37 (d, 2H, J=8.3 Hz), 7.44~7.46 (m, 2H), 7.75 (d, 2H, J=8.4 Hz); ¹³C NMR (100 MHz, CDCl₃): δ 52.3, 115.1, 115.4, 124.0, 126.8, 127.7, 128.0, 129.7, 129.8, 137.4, 135.9, 137.7, 139.2, 141.9, 145.9, 158.7, 163.2; MS (EI) m/z: 432.0 (M⁺, 9.1%), 212.0 (100.0%).

Example 43

Synthesis of 4-(7-pyridin-4-yl-2,3-dihydro-indole-1-sulfonyl)-benzenesulfonamide (Compound 43)

Compound 43 was prepared in a manner similar to that described in Example 17.

Mp: 241.7-242.9° C.; ¹H NMR (500 MHz, CDCl₃): δ 2.33 (t, 2H, J=7.3 Hz), 4.02 (t, 2H, J=7.3 Hz), 7.08 (bd, 1H, J=5.5 Hz), 7.19~7.21 (m, 2H), 7.37 (d, 2H, J=8.2 Hz), 7.47 (d, 2H, J=5.5 Hz), 7.77 (d, 2H, J=8.3 Hz), 8.40 (d, 2H, J=5.5 Hz); MS (EI) m/z: 415.0 (M⁺, 9.1%), 195.1 (100.0%).

Example 44

Synthesis of 1-(4-methoxy-benzenesulfonyl)-7-thiophen-2-yl-1H-pyrrolo[2,3-c]pyridine (Compound 44)

Compound 44 was prepared in a manner similar to that described in Example 6.
Mp: 112.2-113.7° C.; ¹H NMR (500 MHz, CDCl₃): δ 3.78 (s, 3H), 6.70 (d, 1H, J=3.72 Hz), 6.75 (d, 2H, J=8.89 Hz), 7.05 (t, 1H, J=4.34 Hz), 7.28 (d, 2H, J=8.88 Hz), 7.31 (d, 1H, J=5.07 Hz), 7.34 (d, 1H, J=3.88 Hz), 7.43 (d, 1H, J=5.00 Hz), 7.81 (d, 1H, J=3.66 Hz), 8.39 (d, 1H, J=5.07 Hz); MS (EI) m/z: 370.0 (M⁺, 36.0%), 199.1 (100.0%); HRMS (EI) for $C_{18}H_{14}N_2O_3S_2$ (M⁺): calcd, 370.0445; found, 370.0444.

Example 45

Synthesis of 5-[1-(4-methoxy-benzenesulfonyl)-1H-pyrrolo[2,3-c]pyridin-7-yl]-furan-2-carbaldehyde (Compound 45)

Compound 45 was prepared in a manner similar to that described in Example 6.
¹H NMR (500 MHz, CDCl₃): δ 3.80 (s, 3H), 6.74 (d, J=3.7 Hz, 1H), 6.86 (d, J=8.9 Hz, 2H), 6.98 (d, J=3.6 Hz, 1H), 7.40 (d, J=3.6 Hz, 1H), 7.50 (d, J=5.1 Hz, 1H), 7.54 (d, J=8.8 Hz, 2H), 7.70 (d, J=3.6 Hz, 1H), 8.48 (d, J=5.2 Hz, 1H), 9.62 (s, 1H).

Example 46

Synthesis of 1-(4-methoxy-benzenesulfonyl)-7-pyridin-3-yl-2,3-dihydro-1H-indole (Compound 46)

Compound 46 was prepared in a manner similar to that described in Example 17.
Mp: 178.8-181.0° C.; ¹H NMR (500 MHz, CDCl₃): δ 2.22 (t, 2H, J=7.37 Hz), 3.76 (s, 3H), 3.92 (t, 2H, J=7.44 Hz), 6.71 (d, 2H, J=8.83 Hz), 7.01 (d, 1H, J=6.69 Hz), 7.15~7.20 (m, 4H), 7.30 (q, 1H, J=6.33 Hz), 7.93~7.96 (m, 1H), 8.36 (q, 1H, J=4.78 Hz), 8.70 (d, 1H, J=1.83 Hz); MS (EI) m/z: 366.0 (M⁺, 40.7%), 195.1 (100.0%); HRMS (EI) for $C_{20}H_{18}N_2O_3S$ (M⁺): calcd, 366.1038; found, 366.1036.

Example 47

Synthesis of 7-(4-(1H-tetrazol-5-yl)phenyl)-1-(4-methoxyphenylsulfonyl)indoline (Compound 47)

Compound 47 was prepared in a manner similar to that described in Example 17.
¹H NMR (500 MHz, CD₃OD) δ 2.34 (t, J=7.3 Hz, 2H), 3.80 (s, 3H), 4.07 (t, J=7.3 Hz, 2H), 6.88 (d, J=8.8 Hz, 2H), 7.14 (d, J=7.1 Hz, 1H), 7.27-7.37 (m, 4H), 7.84 (d, J=8.3 Hz, 2H), 8.04 (d, J=8.2 Hz, 2H).

Example 48

Synthesis of sodium 4-(1-(4-methoxyphenylsulfonyl)indolin-7-yl)phenyl phosphate (Compound 48)

Compound 48 was prepared in a manner similar to that described in Example 17.

$^1$H NMR (500 MHz, D$_2$O+DMSO-d$_6$) δ 2.38 (t, J=7.2 Hz, 2H), 3.90 (s, 3H), 4.09 (t, J=7.3 Hz, 2H), 7.01 (d, J=8.8 Hz, 2H), 7.20 (d, J=7.2 Hz, 1H), 7.30-7.44 (m, 6H), 7.71 (d, J=8.5 Hz, 2H).

Example 49

Cell Growth Inhibition Assay

Anticancer activities of the aryl substituted sulfonamide compounds synthesized in the above examples were evaluated by testing their inhibitory effects on mammalian cancer cell growth.

Human oral epidermoid carcinoma KB cells, non small cell lung carcinoma H460 cells, colorectal carcinoma HT29 cells, and stomach carcinoma MKN45 cells were maintained in RPMI-1640 medium supplied with 5% fetal bovine serum. The cells were treated with the test compound at various concentrations for 72 h. The effect of the test compound on cell growth was evaluated using a methylene blue dye assay similar to that described in Baguley et al., Anal Biochem, 1984, 139: 272-277. IC$_{50}$ of a test compound (i.e., the concentration of the test compound that results in 50% growth inhibition compared to the control) was then obtained. Compounds 16, 17, and 24 were tested on these three cell lines using methylene blue dye assay. ABT-751 was used as positive control (which was synthesized with the method described in Yoshino et al., J. Med. Chem. 1992, 35, 2496-2497; descriptions of ABT-751 can also be found in Koyanagi et al., Cancer Res. 1994, 54, 1702-1706; Yee et al., Cancer Res. 2005, 11, 6615-6624; and Mauer, et al., J. Thorac. Oncol. 2008, 3, 613-636). Unexpectedly, Compounds 16, 17, and 24 all showed much lower IC$_{50}$ values than ABT-751. See Table 1 below.

TABLE 1

| Compound | Cell type (IC$_{50}$ ± SD$^a$, nM) | | |
|---|---|---|---|
| | KB (oral) | H460 (lung) | MKN45 (stomach) |
| Compound 16 | 21.1 ± 11.2 | 40 ± 14.1 | 27.5 ± 3.5 |
| Compound 17 | 31.1 ± 5.4 | 29.5 ± 14.8 | 17.2 ± 8.6 |
| Compound 24 | 96 ± 14.1 | 101 ± 8 | 69.5 ± 7.6 |
| ABT-751 | 251 ± 65 | 218 ± 4 | 166 ± 8 |

$^a$standard deviation

Further, Compound 24 was tested on non-small-cell lung cancer A549 and H1299 cells, colorectal carcinoma HT29, and normal human umbilical vein endothelial cells (HU-VECs). Unexpectedly, this compound also showed low IC$_{50}$ values against all three cancer cell lines yet a much higher IC$_{50}$ value against the normal HUVECs. See Table 2 below.

TABLE 2

| Origin | Cell Line | Growth Inhibition (IC$_{50}$, nM) |
|---|---|---|
| Non-small-cell lung cancer | A549 | 150 ± 8.5 |
| Non-small-cell lung cancer | H1299 | 132 ± 13.7 |
| Colorectal caricinoma | HT29 | 201 ± 13.9 |
| (Normal cell) Umbilical vein endothelial | HUVEC | 510 ± 22.2 |

Compounds 1-40 and 44 were tested for inhibiting proliferation of human oral epidermoid carcinoma KB cells. Unexpectedly, all of the tested compounds, except Compound 39, have IC$_{50}$ values lower than 4 µM. Among them, Compounds 1, 2, 4-6, 9-11, 13-15, 18-20, 23, 25-27, 30-31, 33-34, and 40 have IC$_{50}$ values between 100 nM and 700 nM; and Compounds 8, 16, 17, 21, 24, 28-29, 36-38 and 44 have IC$_{50}$ values between 1 nM and 99 nM.

Example 50

Cell Growth Inhibition Assay on Multidrug Resistant (MDR) KB Cells

KB-VIN10 cells were maintained in growth medium supplemented with 10 nM vincristine, generated from vincristine-driven selection, and displayed overexpression of P-gp170/MDR. Cell in logarithmic phase were cultured at a density of 5000 cells/mL/well in a 24-well plate. KB-VIN10 cells were cultured in a medium free of test compound for 3 days prior to use. The cells were treated with the test compound at various concentrations for 72 h. The effect of the test compound on cell growth was evaluated using the methylene blue dye assay. IC$_{50}$ of a test compound (i.e., the concentration of the test compound that results in 50% growth inhibition compared to the control) was then obtained. Compounds 16 and 24 were tested in this assay. Unexpectedly, Compounds 16 and 24 have an IC$_{50}$ value of 30 nM and 106 nM, respectively. In comparison, ABT-751 has an IC$_{50}$ value of 385 nM in the same assay.

KB-VIN10 and KB-TAX50 cells were generated by vincristine and paclitaxel-driven selection, respectively, and displayed overexpression of P-gp170/MDR. KB-7D cells were generated by VP-16-driven selection, which displayed down-regulation of Top II and overexpression of MRP. KB-CPT100 and KB-CPT300 cells were generated by camptothecin-driven selection. KB-L30 cells were generated by BPR0L075-driven selection, which displayed mutation of β-tubulin. (See Liou, J. P. et al J. Med. Chem. 2004, 47, 4247-4257 and Kuo, C. C. et al. Cancer Res. 2004, 64, 4621-4628.)

Anticancer activities of the aryl substituted sulfonamide compounds synthesized in the above examples were evaluated by testing their inhibitory effects on these drug-resistant cell lines. Compound 24 was tested in this assay. Unexpectedly, Compound 24 showed IC$_{50}$ values ranging from 90~250 nM (Table 3 below), indicating that this compound is a potent anticancer agent in treating various multiple-drug resistant cancers.

TABLE 3

| Cell Line | Resistance Type | Growth Inhibition (IC$_{50}$, nM) |
|---|---|---|
| KB | (Parental) | 96 ± 14.1 |
| KB-VIN10 | Vincristine resistance | 106 ± 18.0 |
| KB-TAX50 | Paclitaxel resistance | 188 ± 25.3 |
| KB-7D | Etoposide resistance | 257 ± 26.6 |
| KB-L30 | BPR0L075 resistance | 237 ± 26.6 |
| KB-CPT100 | Camptothecin resistance | 95 ± 12.1 |
| KB-CPT300 | Camptothecin resistance | 93 ± 15.7 |

Example 51

Tubulin Polymerization Inhibition Assay

Effects of the aryl substituted sulfonamide compounds on tubulin polymerization were evaluated using turbidimetric assays as described by Bollag et al., *Cancer Res.* 2005, 55, 2325-2333.

Microtubule-associated protein (MAP)-rich tubulin (from bovine brain, Cytoskeleton, Denver, C.O.) was dissolved in reaction buffer (100 mM PIPES, pH 6.9, 2 mM MgCl$_2$, 1 mM GTP) to obtain a 4 mg/mL tubulin solution. The tubulin solution (240 µg MAP-rich tubulin per well) was placed in a 96-well microtiter plate in the presence of a test compound or 2% (v/v) DMSO as vehicle control. The absorbance of the test compound-treated solution was measured at 350 nm in a PowerWave X Microplate Reader (BIO-TEK Instruments, Winooski, Vt.) at 37° C. and recorded every 30 s for 30 min so as to obtain an absorbance curve. The area under the curve (AUC) was then calculated. The tubulin polymerization inhibitory efficacy of a test compound at a certain concentration was evaluated by the following ratio: $(AUC_{100}-AUC)/(AUC_{100}-AUC_0)$, in which $AUC_{100}$ is the area under the curve of the untreated control curve (i.e., corresponding to 100% polymerization) and AUG is the area under the curve of the absorbance curve obtained from 10 µM colchicine (i.e., corresponding to 0% polymerization).

Compounds 16, 17, and 24 were tested in this assay. Unexpectedly, at a concentration of 2.5 µM, the three compounds all showed >50% inhibition of tubulin polymerization.

Example 52

Evaluation of Anti-Angiogenesis Activity

Anti-angiogenesis activities of the aryl substituted sulfonamide compounds were evaluated via the following two assays.

(i) Cellular Network Formation Inhibition Assay

Each well of a 96-well plate was coated with an extracellular matrix containing collagen for 1 hr to allow the gel to solidify. Human umbilical vein endothelial cells (HUVECs) suspension was prepared at a concentration of $1\times10^5$ cells/mL in M199 medium supplemented with endothelial cell growth supplements with 20% FBS. Then, 100 µl of the cell suspension was added to each gel-coated well of the plate. Cells were incubated with or without a test compound for 18 hrs at 37° C. Without the test compound, a cellular network structure was fully developed after 12-18 hrs of incubation. The number of tubes formed was counted using light microscopy at 200× magnification. $IC_{50}$ of a test compound is defined as the concentration of the test compound that results in 50% tube formation inhibition compared to the control.

Compound 24 was tested in this assay. Unexpectedly, Compound 24 showed an $IC_{50}$ of 0.5 and completely inhibited tube formation at 1.5

(ii) VEGF Production Inhibition Assay

The medium of assay (i) above was collected. VEGF165 levels were measure by ELISA. In brief, a monoclonal antibody specific for VEGF was pre-coated onto a microplate. A control cell culture medium and the medium of assay (i) were added into the wells and any VEGF present was bound to the wells by the immobilized antibody. After washing away any unbound substances, an enzyme-linked polyclonal antibody specific for VEGF was added to the wells. Following a wash to remove any unbound antibody-enzyme reagent, a substrate solution was added to the wells and color developed in proportion to the amount of VEGF bound in the initial step. The color development was stopped and the intensity of the color was measured.

It was observed that Compound 24 inhibited more than 50% VEGF production at 0.5 µM.

Example 53

Evaluation of Anti-Vascular Activity

Anti-vascular activities of the aryl substituted sulfonamide compounds were evaluated by immunofluorescence staining in tumor tissues.

Rat anti-mouse CD31 antibodies were purchased from BD Biosciences. Tumor tissue samples were harvested from mice in both the control and test compound-treated groups. Frozen sections were fixed with acetone and chloroform. To block nonspecific proteins, each sample was incubated in 4.5% fish gelatin (BB International Co.) for 20 min. Expression of CD31 was detected in blood vessels using rat anti-mouse CD31 as the primary antibody and TexasRed (Jackson) labeled-goat anti-rat IgG antibody as the secondary antibody. The mean microvessel density (MVD) was determined by first counting and then averaging the number of CD31-positive cells in five random high power microscopic fields from different tumor samples.

Compound 24 was tested in this assay. Unexpectedly, Compound 24 at about 96 nM decreased vascular area five-fold, compared to the blank control.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (II):

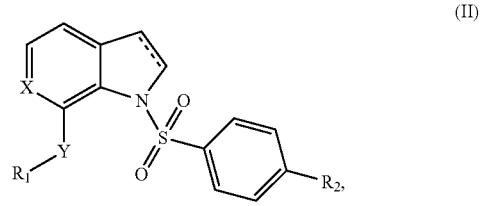

wherein
- - - - is a single bond or a double bond;
X is $CR_a$, in which $R_a$ is H, alkyl, alkenyl, alkynyl, aryl, heteroaryl, cycloalkyl, cycloalkenyl, heterocycloalkyl, or heterocycloalkenyl;
Y is deleted;
$R_1$ is aryl, heteroaryl, cycloalkyl, cycloalkenyl, heterocycloalkyl, or heterocycloalkenyl; and
$R_2$ is alkenyl, alkynyl, aryl, heteroaryl, cycloalkyl, cycloalkenyl, heterocycloalkyl, heterocycloalkenyl, halo, cyano, nitro, $OR_c$, $SO_2NR_cR_d$, $OC(O)R_c$, $C(O)R_c$, $C(O)OR_c$, $C(O)NR_cR_d$, $NR_cR_d$, $NHC(O)R_c$, $NHC(O)NR_cR_d$, or $NHC(S)R_c$, in which each of $R_c$ and $R_d$, independently, is H, alkyl, alkenyl, alkynyl, aryl, heteroaryl, cycloalkyl, cycloalkenyl, heterocycloalkyl, or heterocycloalkenyl.

2. The compound of claim 1, wherein X is CH.

3. The compound of claim 2, wherein $R_1$ is aryl or heteroaryl.

4. The compound of claim 3, wherein $R_2$ is $OR_c$ or $SO_2NR_cR_d$.

5. The compound of claim 4, wherein $R_2$ is $OR_c$ in which $R_c$ is alkyl.

6. The compound of claim 5, wherein $R_1$ is phenyl.

7. A method for inhibiting tubulin polymerization by contacting a cell with an effective amount of a compound of claim 1.

8. A method for treating cancer, comprising administering to a subject in need thereof an effective amount of a compound of claim 1.

9. A pharmaceutical composition, comprising a compound of claim 1 and a pharmaceutically acceptable carrier.

10. The compound of claim 5, wherein $R_1$ is heteroaryl.

* * * * *